(12) United States Patent
Chiodo et al.

(10) Patent No.: US 10,045,998 B2
(45) Date of Patent: Aug. 14, 2018

(54) SOLID FORM OF ABIRATERONE ACETATE

(71) Applicant: BASF SE, Ludwigshafen (DE)

(72) Inventors: Tiziana Chiodo, Mannheim (DE); Beate Salvador, Ellerstadt (DE); Marcus Vossen, Limburgerhof (DE); Andreas Hafner, Gelterkinden (CH); Tobias Hintermann, Therwil (CH); Martin Szelagiewicz, Basel (CH); Fritz Blatter, Reinach (CH); Martin Viertelhaus, Mannheim (DE); Walter Weishaar, Gruenstadt (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/103,146

(22) PCT Filed: Dec. 9, 2014

(86) PCT No.: PCT/EP2014/077044
§ 371 (c)(1),
(2) Date: Jun. 9, 2016

(87) PCT Pub. No.: WO2015/086596
PCT Pub. Date: Jun. 18, 2015

(65) Prior Publication Data
US 2016/0303143 A1 Oct. 20, 2016

(30) Foreign Application Priority Data
Dec. 12, 2013 (EP) .................................. 13196835

(51) Int. Cl.
*A61K 31/58* (2006.01)
*A61K 9/14* (2006.01)
*C07J 43/00* (2006.01)

(52) U.S. Cl.
CPC ................ *A61K 31/58* (2013.01); *A61K 9/14* (2013.01); *C07J 43/003* (2013.01); *C07B 2200/13* (2013.01)

(58) Field of Classification Search
CPC ......... A61K 9/14; A61K 31/58; C07J 43/003; C07B 2200/13
See application file for complete search history.

(56) References Cited

U.S. PATENT DOCUMENTS 5,604,213 A 2/1997 Barrie et al.
2007/0249836 A1 10/2007 Hunt
(Continued)

FOREIGN PATENT DOCUMENTS

| CN | 102336801 A | 2/2012 |
|---|---|---|
| CN | 103059090 A | 4/2013 |

(Continued)

OTHER PUBLICATIONS

Ichim et al. Journal of Translational Medicine 2011, 9:25.*
(Continued)

*Primary Examiner* — Angela C Brown-Pettigrew
(74) *Attorney, Agent, or Firm* — Oblon, McClelland, Maier & Neustadt, L.L.P.

(57) ABSTRACT

Combinations of (3β)-17-(pyridin-3-yl)androsta-5,16-dien-3-yl acetate (Abiraterone acetate) with acidic substances such as citric acid, ascorbic acid, methyl-4-hydroxy benzoate, saccharin, vanillic acid, adipic acid, maleic acid, malic acid, tartaric acid are useful as pharmaceutical preparations and show improved properties such as aqueous solubility and dissolution kinetics, especially in the form of cocrystals or their combination with a suitable acid.

6 Claims, 15 Drawing Sheets

(56) References Cited

U.S. PATENT DOCUMENTS

| | | | |
|---|---|---|---|
| 2009/0124587 A1* | 5/2009 | Auerbach | A61K 31/58 |
| | | | 514/176 |
| 2010/0152437 A1 | 6/2010 | Hunt | |
| 2012/0053340 A1 | 3/2012 | Hunt | |
| 2013/0090468 A1 | 4/2013 | Hunt | |
| 2014/0287039 A1 | 9/2014 | Bosch et al. | |
| 2014/0288037 A1 | 9/2014 | Casebier et al. | |

FOREIGN PATENT DOCUMENTS

| | | |
|---|---|---|
| WO | WO 2006/021776 A1 | 3/2006 |
| WO | WO 2013/012959 A1 | 1/2013 |
| WO | WO 2014/009436 A1 | 1/2014 |
| WO | WO 2014/083512 A1 | 6/2014 |
| WO | WO 2014/145813 A1 | 9/2014 |
| WO | WO 2015/000451 A1 | 1/2015 |

OTHER PUBLICATIONS https://labs.chem.ucsb.edu/zhang/liming/pdf/pKas_of_Organic_Acids_and_Bases.pdf, accessed Jul. 5, 2017.*
International Search Report dated Feb. 19, 2015 in PCT/EP2014/077044 filed Dec. 9, 2014.
European Medicines Agency, Science Medicines Health, Assessment Report for Zytiga (abiraterone), Procedure No. EMEA/H/C/002321, Committee for Medicinal Products for Human Use (CHMP), Jul. 21, 2011, EMA/CHMP/542871/2011, 78 pages.

* cited by examiner

SOLID FORM OF ABIRATERONE ACETATE

The present invention provides a method for improving the solubility of abiraterone acetate in aqueous environments, to solid pharmaceutical compositions comprising abiraterone acetate and certain organic acids, to novel cocrystals comprising abiraterone acetate and certain organic acids, as well as to pharmaceutical uses of the compositions and cocrystals e.g. in the treatment of androgen- or oestrogen-dependent disorders.

U.S. Pat. No. 5,604,213 discloses abiraterone acetate, which is the synonym for (3β)-17-(3-pyridinyl)androsta-5,16-dien-3-yl acetate specifically shown in formula (1):

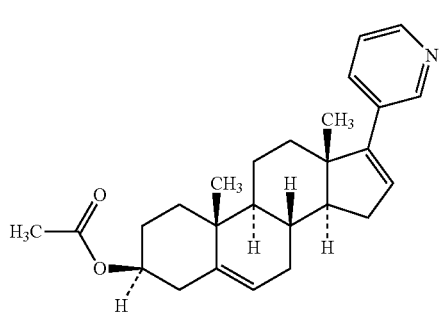

(1)

Abiraterone acetate is the prodrug of abiraterone of the formula (2)

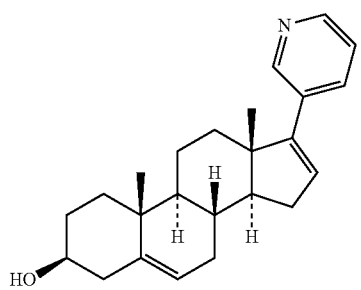

(2)

which is known as an inhibitor of CYP17 (17α-hydroxylase/C17,20-lyase). Abiraterone acetate is marketed under the trade name ZYTIGA® by Janssen Biotech (Johnson & Johnson). It is applied orally to treat hormone-resistant or hormone-refractory prostate cancer. Abiraterone acetate is a class IV drug (low solubility and low permeability) according to the biopharmaceutics classification system (BCS) showing only very low solubility (see report EMA/CHMP/542871/2011). More recent publications report quick absorption (median peak concentration 2 h after dosing) of a small fraction of the dose, while the major portion passes the intestine without metabolism. Solubility of the prodrug in aqueous environments, such as gastric or intestinal environment, thus appears to be critical for its bioavailability.

A crystalline form of abiraterone acetate is published in IPCOM000211139D of Sep. 22, 2011, and CN-A-102336801. WO 2006/021776 investigates the formation of solid salts from solutions of abiraterone acetate with tartaric, acetic, malic or methanesulfonic acid for purification purposes.

It has now been found that the aqueous solubility of abiraterone acetate, especially the solubility in a gastric or intestinal environment, may be distinctly enhanced by combining this prodrug with certain organic acids.

It has further been found that certain salts, and certain cocrystals, of abiraterone acetate solids show advantageous properties for use as medical application forms of abiraterone acetate. Preferred ones among these solid forms are those comprising abiraterone acetate and the organic acid within the same crystalline phase (i.e. the organic acid forming a crystalline salt or cocrystal with abiraterone acetate, such organic acids are also recalled as "coformer" in the following). According to the invention, the organic acid (especially the coformer) is selected from the group consisting of citric acid, methyl-4-hydroxy benzoate, saccharin, vanillic acid, adipic acid, maleic acid, malic acid, and tartaric acid. Tartaric acid typically is L-tartaric acid; malic acid typically is D,L-malic acid.

The term "acid" as used herein stands for a compound or ion acting as proton donor (i.e. Broensted acid). The term "organic acid" as used herein generally denotes an acid comprising carbon-hydrogen bonds.

The present organic acids useful as coformers are solid at ambient temperature (i.e. are solids under standard conditions 20° C. and normal atmospheric pressure); when used as coformers, these acids are able to modulate relevant solid state properties of the active agent abiraterone acetate and thus of its solid dosage form (e.g. by reducing hygroscopicy, improving storage stability), and to modulate its dissolution properties and bioavailability, e.g. by effecting the microenvironment of the drug particles during the dissolution process.

Existing solid forms of abiraterone acetate leave room for improvement of physical as well as biological characteristics. There exists a need for other solid forms, especially crystalline forms, of (3β)-17-(3-pyridinyl)androsta-5,16-dien-3-yl acetate for sufficient diversity on crystalline materials to optimize manufacture, formulation and biological efficiency and to control its complex polymorphism.

SUMMARY OF THE INVENTION

The invention provides a method for enhancing the solubility and dissolution rate of the active agent (3β)-17-(pyridin-3-yl)androsta-5,16-dien-3-yl acetate in aqueous environments by contacting the active agent with one or more pharmaceutically acceptable organic acids of pKa less than 5.0, especially from the range 4.9-1.1. According to the present invention, the organic acid is preferably selected from the group consisting of citric acid, ascorbic acid, methyl-4-hydroxy benzoate, saccharin, vanillic acid, adipic acid, maleic acid, malic acid, and tartaric acid.

Consequently, the present invention further pertains to the use of a pharmaceutically acceptable organic acid, which is typically selected from organic acids which are solid under standard conditions, and which is characterized by a pKa of less than 5.0, especially from the range 4.9-1.1, for enhancing the solubility and/or enhancing the bioavailability of the active agent (3β)-17-(pyridin-3-yl)androsta-5,16-dien-3-yl acetate in aqueous environments, where the organic acid is preferably selected from the group consisting of citric acid, ascorbic acid, methyl-4-hydroxy benzoate, saccharin, vanillic acid, adipic acid, maleic acid, malic acid, and tartaric acid; as well as to a pharmaceutical composition comprising 3β)-17-(pyridin-3-yl)androsta-5,16-dien-3-yl acetate and one or more pharmaceutically acceptable organic acids of pKa less than 5.0, especially from the range 4.9-1.1, which organic acids are preferably selected from the group consisting of citric acid, ascorbic acid, methyl-4-hydroxy benzoate, saccharin, vanillic acid, adipic acid, maleic acid, malic acid, and tartaric acid, and a pharmaceutically acceptable carrier or diluent.

Especially preferred is a method for enhancing the solubility and dissolution rate of the active agent as described above, by contacting with the ascorbic acid as the organic acid, or by contacting with ascorbic acid in combination with an acid selected from the group consisting of citric acid, methyl-4-hydroxy benzoate, saccharin, vanillic acid, adipic acid, maleic acid, malic acid, and tartaric acid, the latter for example in form of the crystalline solid described below. Consequently, the use of ascorbic acid for enhancing the solubility and/or enhancing the bioavailability of Abiraterobe acetate, as descrbed above, is an especially preferred use of an organic acid accordint to the invention.

Certain organic acids have been found to form crystalline solids with (3β)-17-(pyridin-3-yl)androsta-5,16-dien-3-yl acetate. The present invention thus further pertains to a pharmaceutical composition comprising a crystalline material or multicomponent molecular crystal and a pharmaceutically acceptable carrier or diluent, characterized in that the crystalline material or multicomponent molecular crystal comprises (3β)-17-(pyridin-3-yl)androsta-5,16-dien-3-yl acetate and an organic acid selected from the group consisting of citric acid, methyl-4-hydroxy benzoate, saccharin, vanillic acid, adipic acid, maleic acid, malic acid, and tartaric acid.

The present invention further pertains to a novel multicomponent molecular crystal comprising (3β)-17-(pyridin-3-yl)androsta-5,16-dien-3-yl acetate and an organic acid within the same crystalline phase, the organic acid being selected from the group consisting of citric acid, methyl-4-hydroxy benzoate, saccharin, vanillic acid, adipic acid, and maleic acid, especially selected from the group consisting of methyl-4-hydroxy benzoate, saccharin, vanillic acid, adipic acid, and maleic acid.

Said crystalline forms show desired different physical and/or biological characteristics which may assist in the manufacture or formulation of the active compound, to the purity levels and uniformity required for regulatory approval. The said crystalline form may possess improved pharmacological characteristics, for example, improved bioavailability, thus offering enhanced possibilities to modulate and design improved drug products.

DETAILED DESCRIPTION OF THE INVENTION

The present method for enhancing the solubility of (3β)-17-(pyridin-3-yl)androsta-5,16-dien-3-yl acetate in an aqueous environment comprises contacting (3β)-17-(pyridin-3-yl)androsta-5,16-dien-3-yl acetate with one or more pharmaceutically acceptable organic acids of pKa less than 5.0, especially from the range 4.9-1.1.

pKa denotes the negative logarithm of the acid's dissociation constant Ka, the logarithm being to the base 10.

For use in the method of the invention, organic acids are preferably selected from the group consisting of citric acid, ascorbic acid, methyl-4-hydroxy benzoate, saccharin, vanillic acid, adipic acid, maleic acid, malic acid, and tartaric acid. An advantageous method comprises contacting a crystalline material or multicomponent molecular crystal comprising (3β)-17-(pyridin-3-yl)androsta-5,16-dien-3-yl acetate and an organic acid typically selected from the group consisting of citric acid, methyl-4-hydroxy benzoate, saccharin, vanillic acid, adipic acid, maleic acid, malic acid, and tartaric acid, within the same crystalline phase, with one or more additional organic acid component, whose organic acid preferably comprises citric acid and/or ascorbic acid, especially ascorbic acid.

For enhancing the aqueous solubility and/or bioavailability of the prodrug, the amount of organic acid chosen usually is at least 0.9 molar equivalents on 1 molar equivalent of (3β)-17-(pyridin-3-yl)androsta-5,16-dien-3-yl acetate, especially 0.9 to 10 molar equivalents organic acid on 1 molar equivalent of (3β)-17-(pyridin-3-yl)androsta-5,16-dien-3-yl acetate.

The present invention provides pharmaceutical compositions comprising a solid essentially consisting of abiraterone acetate and one coformer selected from the group consisting of adipic acid, citric acid, D,L-malic acid, maleic acid, methyl-4-hydroxy benzoate, saccharin, L-tartaric acid, and vanillic acid, especially of adipic acid, D,L-malic acid, maleic acid, methyl-4-hydroxy benzoate, saccharin, L-tartaric acid, and vanillic acid, more especially of adipic acid, maleic acid, methyl-4-hydroxy benzoate, saccharin, acid, and vanillic acid.

In the guidance for pharmaceutical cocrystals provided by the US food and drug administration (FDA), the following criterion is stated: If the active pharmaceutic ingredient (API) and the coformer differ in their pKa (pKa (conjugated base)-pKa (acid)) by more than 1, there will be substantial proton transfer resulting in ionization and formation of a salt rather than a co-crystal; on the other hand, if API and coformer differ in their pKa (pKa (base)-pKa (acid)) by less than 1, the active ingredient-coformer solid complex may be classified as a cocrystal. The present solid forms, in the following summarized as multicomponent molecular crystal, thus may be classified as cocrystals or crystalline salts of abiraterone acetate. The present multi-component molecular crystal typically comprises (3β)-17-(pyridin-3-yl)androsta-5,16-dien-3-yl acetate and the organic acid within the same crystalline phase in a molar ratio ranging from from 2.1:1 to 1:2.1, in particular from 1.5:1 to 1:1.5, and especially from 1.1:1 to 1:1.1.

Multi-component molecular crystals for use according to the present invention comprise (3β)-17-(pyridin-3-yl)androsta-5,16-dien-3-yl acetate and a coformer; the crystals show show a characteristic X-ray powder diffraction pattern [with typical peak intensities indicated in brackets; (vs) standing for very strong, (s) standing for strong, (m) standing for medium, (w) standing for weak, and (vw) standing for very weak)]:

Where the coformer is citric acid, the crystalline phase comprising (3β)-17-(pyridin-3-yl)androsta-5,16-dien-3-yl acetate and the coformer exhibits a X-ray powder diffraction pattern with the characteristic peaks, expressed in d-values (Å), 17.6 (m), 11.5 (m), 7.1 (m), 6.4 (m), 6.2 (m), 5.22 (m), 5.14 (vs), 4.57 (vs), 3.44 (s).

Where the coformer is methyl-4-hydroxy benzoate, the crystalline phase form A comprising (3β)-17-(pyridin-3-yl)androsta-5,16-dien-3-yl acetate and the coformer exhibits a X-ray powder diffraction pattern with the characteristic peaks, expressed in d-values (Å), 10.7 (w), 9.2 (s), 7.8 (w), 5.15 (m), 4.93 (s), 4.84 (vs), 4.38 (m), 3.89 (m), 3.28 (m); or the crystalline phase is form B comprising (3β)-17-(pyridin-3-yl)androsta-5,16-dien-3-yl acetate and the coformer and exhibits a X-ray powder diffraction pattern with the characteristic peaks, expressed in d-values (Å), 5.02 (m), 4.80 (s), 4.72 (vs), 4.29 (s), 4.17 (m), 3.81 (s), 3.59 (m), 3.47 (m), 3.23 (s), 3.02 (m);
or the crystalline phase is form C comprising (3β)-17-(pyridin-3-yl)androsta-5,16-dien-3-yl acetate and the coformer and exhibits, as calculated using Mercury CSD 3.3

(Cambridge Crystallographic Data Centre) and using the single crystal data shown further below, a X-ray powder diffraction pattern with the characteristic peaks, expressed in d-values (Å), at a temperature of 100 K, at 6.2 (m), 15.1 (s), 15.4 (s), 16.8 (s), 20.3 (vs), 23.2 (m).

Where the coformer is saccharin, the crystalline phase comprising (3β)-17-(pyridin-3-yl)androsta-5,16-dien-3-yl acetate and the coformer exhibits a X-ray powder diffraction pattern with the characteristic peaks, expressed in d-values (Å), 13.5 (w), 10.0 (m), 6.7 (vs), 6.5 (s), 5.99 (s), 5.74 (m), 5.36 (s), 5.05 (s), 4.35 (s), 4.28 (vs), 3.72 (s), 3.41 (s).

Where the coformer is vanillic acid, the crystalline phase comprising (3β)-17-(pyridin-3-yl)androsta-5,16-dien-3-yl acetate and the coformer exhibits a X-ray powder diffraction pattern with the characteristic peaks, expressed in d-values (Å), 13.5 (w), 6.8 (m), 6.4 (m), 4.51 (vs), 4.15 (vs), 3.20 (s).

Where the coformer is adipic acid, the crystalline phase comprising (3β)-17-(pyridin-3-yl)androsta-5,16-dien-3-yl acetate and the coformer exhibits a X-ray powder diffraction pattern with the characteristic peaks, expressed in d-values (Å), 9.0 (m), 6.2 (m), 5.63 (vs), 5.30 (s), 4.90 (s), 4.47 (s), 4.07 (s), 3.71 (s).

Where the coformer is maleic acid, the crystalline phase comprising (3β)-17-(pyridin-3-yl)androsta-5,16-dien-3-yl acetate and the coformer (form A) exhibits a X-ray powder diffraction pattern with the characteristic peaks, expressed in d-values (Å), 13.7 (w), 10.2 (w), 7.7 (m), 6.6 (vs), 6.1 (s), 5.03 (vs), 4.46 (m), 4.26 (m), 3.88 (m);
or (form B) exhibits a X-ray powder diffraction pattern with the characteristic peaks, expressed in d-values (Å), 14.1 (w), 10.4 (w), 7.8 (m), 6.7 (s), 6.2 (s), 5.74 (m), 5.27 (s), 5.08 (vs), 5.04 (s), 4.82 (s), 4.51 (s), 4.30 (s), 3.91 (s), 3.39 (s);
or (form C) exhibits a X-ray powder diffraction pattern with the characteristic peaks, expressed in d-values (Å), 24.0 (vw), 20.8 (vw), 10.8 (vs), 8.7 (s), 5.61 (s), 5.42 (s), 5.36 (m), 5.21 (vs), 4.95 (s), 4.38 (s), 3.77 (s);
or (form D) exhibits a X-ray powder diffraction pattern with the characteristic peaks, expressed in d-values (Å), 17.2 (w), 6.7 (m), 6.0 (vs), 5.36 (s), 5.08 (s), 4.58 (s), 4.17 (s), 3.59 (w).

Where the coformer is D,L-malic acid, the crystalline phase comprising (3β)-17-(pyridin-3-yl)androsta-5,16-dien-3-yl acetate and the coformer exhibits a X-ray powder diffraction pattern with the characteristic peaks, expressed in d-values (Å), 20.2 (m), 10.2 (m), 7.6 (w), 6.6 (m), 5.80 (w), 5.46 (m), 5.37 (m), 5.23 (vs), 5.11 (m), 5.03 (m), 4.95 (m), 4.68 (m), 4.53 (m), 4.17 (m).

Where the coformer is L-tartaric acid, the crystalline phase comprising (3β)-17-(pyridin-3-yl)androsta-5,16-dien-3-yl acetate and the coformer (form A) exhibits a X-ray powder diffraction pattern with the characteristic peaks, expressed in d-values (Å), 18.0 (m), 6.8 (w), 5.85 (m), 5.63 (s), 5.21 (m), 5.12 (vs), 4.89 (vs), 4.15 (s), 3.77 (s);
or (form B) exhibits a X-ray powder diffraction pattern with the characteristic peaks, expressed in d-values (Å), 17.0 (s), 11.2 (vs), 6.1 (s), 5.84 (s), 5.59 (vs), 5.49 (s), 5.43 (s), 4.05 (vs), 3.98 (s);
or (form C) exhibits a X-ray powder diffraction pattern with the characteristic peaks, expressed in d-values (Å), 21.1 (s), 10.6 (s), 10.0 (s), 6.5 (s), 5.47 (s), 5.29 (vs), 5.22 (s), 5.11 (vs), 5.01 (vs), 4.83 (s), 4.42 (s), 4.33 (s).

More details of the crystal characteristics of the present multicomponent molecular crystals, and the method of their detection, are given in the examples further below.

1 Å [Angstroem] denotes the length of $10^{-10}$ m.

Another object of the invention is a process for the preparation of a crystalline form as defined above which comprises the steps of
a) combining abiraterone acetate and the organic acid, which acts as the cocrystal former, in a suitable solvent,
b) agitating the mixture obtained in step (a), and
c) separating the solid material and drying.

Abiraterone acetate for combining with the coformer in step (a) may be in any form, for example in the form I as described further below. In process variant of special technical importance, seed crystals of the desired product are added during step (b), typically in an amount of 0.1 to 10% b.w. of the solids.

The solvent used in step (a) is suitably selected according to the solubility of abiraterone acetate and of the co-crystal former. Solvent according to step (a) preferably is a solvent or solvent system wherein each of the components abiraterone acetate and the co-crystal former have a similar solubility. Thus, step (a) typically leads, at least in part, to a dissolution of each of the components (herein recalled as suspension in case that no complete dissolution is effected). Step (a) may result in a suspension of the 2 components, or in a suspension of one component in a solution of the other component, or in a solution of both components; preferred is a solution of both components, and especially a suspension of both components.

The concentration of abiraterone acetate in step (a) may typically range from 0.1 to about 300 mg/ml of solvent (including water), preferably from 20 to 200 mg/ml.

The process is preferably carried out in the temperature range 15-90° C., for example at ambient temperature. In a preferred process, step (c) is carried out at a temperature from the range 30-60° C. or the mixture is heated to a temperature from said range, e.g. about 50° C., especially in case that solid abiraterone acetate is provided in step (a), with forming a solution. The solution thus tempered is then preferably cooled before step (c), i.e. before separation.

Ambient temperature means in the context of the invention a temperature range from room temperature to about 30° C., comprising e.g. 20 to 30° C. and preferably about 23 to 26° C.

The multicomponent molecular crystal of the invention is isolated e.g. by decantation of the liquid, centrifugation and/or filtering off the crystals, which are subsequently dried, e.g. in vacuum, inert gas flow or both, typically at ambient temperature or elevated temperatures up to 80° C.

Besides by agitation and/or crystallization in a solvent, the present multicomponent molecular crystals and/or salts may also be prepared by dry mixing of the educts abiraterone acetate (especially in its form I) and coformer, and grinding the solids in presence of small amounts of a solvent ("solvent drop grinding method").

The currently best procedure to produce the co-crystal obtained with methyl-4-hydroxy benzoate is to dissolve one equivalent of each educt in a mixture of heptane-ethyl acetate 2:1 at about 60° C. then cool to room temperature and equilibrate for a certain time. Further favourable methods for preparing the present abiraterone acetate multicomponent molecular crystal and/or salts are described in more detail in the present examples.

Multicomponent molecular crystals of the invention enable to improve the dissolution characteristics of abiraterone acetate, i.e. providing a better dissolution kinetic profile with respect to the previously known abiraterone acetate.

The present multicomponent molecular crystals are thermodynamically stable and can be dried at elevated temperatures, e.g. below 80° C., and are obtained as a fine powder with typical particle size distributions with the median size between 1 and 50 µm, preferably between 1 to 10 µm. This particle size range ensures a fast dissolution profile, while retaining the favourable handling properties in the formulation process.

The multicomponent molecular crystal of the invention provides good storage stability and is easy to formulate. Multicomponent molecular crystal as defined above generally contains minor amounts of water, mainly within its crystal structure, the amounts usually being up to 5%, for example ranging from 1.5 to 5% of water, relative to the total weight of the solid phase.

Multicomponent molecular crystals of the present invention may be used in pharmaceutical compositions in the same way as other forms of abiraterone acetate previously known.

The present invention also provides a pharmaceutical composition which comprises a therapeutically effective amount of a compound of the invention, in association with a therapeutically acceptable carrier or diluent. The composition of the invention can, for example, be in a form suitable for parenteral (e.g. intravenous, intramuscular or intracavital), oral, topical or rectal administration. Particular forms of the composition may be, for example, solutions, suspensions, emulsions, creams, tablets, capsules, liposomes or micro-reservoirs, especially compositions in orally ingestible or sterile injectable form. The preferred form of composition contemplated is the dry solid form, which includes capsules, granules, tablets, pills, boluses and powders. The solid carrier may comprise one or more excipients, e.g. lactose, fillers, disintegrating agents, binders, e.g. cellulose, carboxymethylcellulose or starch or anti-stick agents, e.g. magnesium stearate, to prevent tablets from adhering to tabletting equipment. Tablets, pills and boluses may be formed so as to disintegrate rapidly or to provide slow release of the active ingredient.

The amount of solid (especially crystalline) forms of abirateroneacetate and hydrates thereof substantially depends on type of formulation and desired dosages during administration time periods. The amount in an oral formulation may be from 10 to 1000 mg, preferably from 50 to 800 mg, and more preferably from 100 to 500 mg.

Oral formulations may be solid formulations such as capsules, tablets, pills and troches, or liquid formulations such as aqueous suspensions, elixirs and syrups. Solid and liquid formulations encompass also incorporation of the present solid form liquid or solid food.

The solid forms according to the invention may be directly used as powders (micronized particles), granules, suspensions or solutions, or they may be combined together with other pharmaceutically acceptable ingredients in admixing the components and optionally finely divide them, and then filling capsules, composed for example from hard or soft gelatine, compressing tablets, pills or troches, or suspend or dissolve them in carriers for suspensions, elixirs and syrups. Coatings may be applied after compression to form pills.

Pharmaceutically acceptable ingredients are well known for the various types of formulation and may be for example binders such as natural or synthetic polymers, excipients, lubricants, surfactants, sweetening and flavouring agents, coating materials, preservatives, dyes, thickeners, adjuvants, antimicrobial agents and carriers for the various formulation types.

Examples for binders are gum tragacanth, acacia, starch, gelatine, and biological degradable polymers such as homo- or co-polyesters of dicarboxylic acids, alkylene glycols, polyalkylene glycols and/or aliphatic hydroxyl carboxylic acids; homo- or co-polyamides of dicarboxylic acids, alkylene diamines, and/or aliphatic amino carboxylic acids; corresponding polyester-polyamide-co-polymers, polyanhydrides, polyorthoesters, polyphosphazene and polycarbonates. The biological degradable polymers may be linear, branched or crosslinked. Specific examples are poly-glycolic acid, poly-lactic acid, and poly-d,l-lactide/glycolide. Other examples for polymers are water-soluble polymers such as polyoxaalkylenes (polyoxaethylene, polyoxapropylene and mixed polymers thereof, poly-acrylamides and hydroxylalkylated polyacrylamides, poly-maleic acid and esters or -amides thereof, poly-acrylic acid and esters or -amides thereof, poly-vinylalcohol und esters or -ethers thereof, poly-vinylimidazole, poly-vinylpyrrolidon, und natural polymers like chitosan, carragenan or hyaluronic aid.

Examples for excipients are phosphates such as dicalcium phosphate.

Examples for lubricants are natural or synthetic oils, fats, waxes, or fatty acid salts like magnesium stearate.

Surfactants may be anionic, anionic, amphoteric or neutral. Examples for surfactants are lecithin, phospholipids, octyl sulfate, decyl sulfate, dodecyl sulfate, tetradecyl sulfate, hexadecyl sulfate and octadecyl sulfate, Na oleate or Na caprate, 1-acylaminoethane-2-sulfonic acids, such as 1-octanoylaminoethane-2-sulfonic acid, 1-decanoylaminoethane-2-sulfonic acid, 1-dodecanoylaminoethane-2-sulfonic acid, 1-tetradecanoylaminoethane-2-sulfonic acid, 1-hexadecanoylaminoethane-2-sulfonic acid, and 1-octadecanoylaminoethane-2-sulfonic acid, and taurocholic acid and taurodeoxycholic acid, bile acids and their salts, such as cholic acid, deoxycholic acid and sodium glycocholates, sodium caprate or sodium laurate, sodium oleate, sodium lauryl sulphate, sodium cetyl sulphate, sulfated castor oil and sodium dioctylsulfosuccinate, cocamidopropylbetaine and laurylbetaine, fatty alcohols, cholesterols, glycerol mono- or -distearate, glycerol mono- or -dioleate and glycerol mono- or -dipalmitate, and poly-oxyethylene stearate.

Examples for sweetening agents are sucrose, fructose, lactose or aspartam.

Examples for flavouring agents are peppermint, oil of wintergreen or fruit flavours like cherry or orange flavour.

Examples for coating materials gelatine, wax, shellac, sugar or biological degradable polymers.

Examples for preservatives are methyl or propylparabens, sorbic acid, chlorobutanol, phenol and thimerosal.

Examples for adjuvants are fragrances.

Examples for thickeners are synthetic polymers, fatty acids and fatty acid salts and esters and fatty alcohols.

Examples for liquid carriers are water, alcohols such as ethanol, glycerol, propylene glycol, liquid polyethylene glycols, triacetin and oils. Examples for solid carriers are talc, clay, microcrystalline cellulose, silica, alumina and the like.

The formulation according to the invention may also contain isotonic agents, such as sugars, buffers or sodium chloride.

The solid forms according to the invention may also be formulated as effervescent tablet or powder, which disintegrate in an aqueous environment to provide a drinking solution.

A syrup or elixir may contain the polymorph of the invention, sucrose or fructose as sweetening agent a preservative like methylparaben, a dye and a flavouring agent.

The dosages include dosages suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The dosages may be conveniently presented in unit dosage form and prepared by any of the methods well known in the art of pharmacy.

Dosage forms include solid dosage forms, like tablets, powders, capsules, suppositories, sachets, troches and losenges as well as liquid suspensions and elixirs. While the description is not intended to be limiting, the invention is also not intended to pertain to true solutions of abirateroneacetate whereupon the properties that distinguish the solid forms of abirateroneacetate are lost. However, the use of the novel forms to prepare such solutions is considered to be within the contemplation of the invention.

Capsule dosages, of course, will contain the solid composition within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric coating.

Slow release formulations may also be prepared from the crystal form according to the invention in order to achieve a controlled release of the active agent in contact with the body fluids in the gastro intestinal tract, and to provide a substantial constant and effective level of the active agent in the blood plasma. The crystal forms may be embedded for this purpose in a polymer matrix of a biological degradable polymer, a water-soluble polymer or a mixture of both, and optionally suitable surfactants. Embedding can mean in this context the incorporation of micro-particles in a matrix of polymers. Controlled release formulations are also obtained through encapsulation of dispersed micro-particles or emulsified micro-droplets via known dispersion or emulsion coating technologies.

The crystal forms of this invention and its formulations respectively can be also administered in combination with other therapeutic agents that are effective to treat a given condition to provide a combination therapy.

The crystal forms of this invention can e.g. be administered in combination with prednisone.

The present invention also includes a method of treating androgen- and oestrogen-dependent disorders, especially tumours, and most especially pro static tumours, in the mammalian body, which comprises administering a compound of the invention to a mammalian patient in a therapeutically effective dose, e.g. in the range 0.001-0.1 mmole/kg body weight, preferably 0.001-0.05 mmole/kg, administered daily or twice daily during the course of treatment. This works out (for humans) at 20-2000 mg/patient per day. The preferred use is in treating prostatic cancer. Another use is in treating breast cancer.

The crystalline forms of the invention may be used as single component or as mixtures with other solid forms.

The following examples illustrate the invention.

Wherever noted, room temperature (r.t.) depicts a temperature from the range 22-25° C.; percentages are given by weight, if not indicated otherwise.

Abbreviations used in in the examples or in the above specification:

Å the length $10^{-10}$ m (Angstroem)
DSC differential scanning calorimetry
DVS dynamic vapor sorption
FTIR Fourier-transformation infrared spectrometry
HPLC high pressure liquid chromatography
H-NMR proton nuclear magnetic resonance
LOD limit of detection
PXRD powder X-ray diffraction
r.h. relative humidity (air, if not indicated otherwise)
TG thermogravimetry
v/v volume by volume
Instrumental Powder X-ray diffraction (PXRD) is carried out with a Bruker D8 (G.16.SYS.S013; Reflection geometry, Bragg-Brentano; Copper K-alpha radiation, 40 kV/40 mA; variable divergence slit; LynxEye detector with 3° window; step size 0.02° (2□); step time 37 s; samples are rotated (0.5 rps) during the measurement) or Panalytical X'Pert Pro diffractometer (using Cu Kα radiation in the Bragg-Brentano reflection geometry, 45 kV and 40 mA, range from 2θ=3°-35°, samples were rotated during the measurement). 2θ values are accurate within an error margin of ±0.1-0.2°.

The samples are prepared without any special treatment other than the application of slight pressure to get a flat surface. The XRPD diffractograms are collected at room temperature with increments of 0.0167°.

Thermogravimetry (TG): Thermogravimetric measurements are carried out with a Netzsch Thermo-Microbalance TG 209 coupled to a Bruker FTIR Spectrometer Vector 22 (TG-FTIR; sample pans with a pinhole, N2 atmosphere, heating rate 10 K/min), or on a Seico TG/DTA 7200 (platinum crucibles under a nitrogen atmosphere and at a heating rate of 10° C./min over the range 30-410° C. or below).

DSC is performed with a Perkin Elmer DSC-7 instrument (closed gold sample pan or gold-plated steel sample pan, heating rates 10 and 20 K/min) or Mettler Toledo DSC 823e module (crimped but vented aluminum pans under nitrogen stream of 150 mL/min and at a heating rate of 10° C./min).

H-NMR: The 1H-NMR spectra are recorded on a Bruker DPX 300 or DRX 500 spectrometer. Solvent: dmso-d6.

DVS: Dynamic (water) vapour sorption (DVS) is performed with a SPS11-100n ("Sorptions Prüfsystem" moisture sorption instrument from Projekt Meßtechnik, Ulm, Germany, using about 20 mg of sample material in an aluminum pan with a change rate of 5% of total relative humidity per hour. Program starting value of 50% with equilibration for 2 hours, continuously lowering to 0%, equilibration (i.e. humidity kept constant), scanning from 0% to 95%, equilibration, scanning from 95% to 0%, equilibration, scanning from 0% to 95%, equilibration, and scanning to 50% relative humidity. Sample temp. 25° C.

Experimental

Solvents: For all experiments, Fluka or Merck analytical grade solvents are used.

Educts:

Adipic acid (hexanedioic acid, Mw 146.14 g/mol; Fluka 02130 puriss. (HPLC));

citric acid (C6H8O7, Mw 192.12 g/mol; Fluka 27488);

D,L-malic acid (Aldrich 240176);

maleic acid (Fluka 63180);

methyl-4-hydroxy benzoate (C8H8O3, Mw 152.15 g/mol; Fluka 54750);

Saccharin (Fluka—12475, purum);

L-tartaric acid (C4H6O6, Mw 150.09 g/mol; Fluka 95310);

vanillic acid (Fluka 94770).

The starting material of abiraterone acetate (C26H33NO2, 391.55 g/mol), obtained from Sinogrand Pharma Ltd., is characterized by H-NMR spectroscopy, powder X-ray diffraction, TG and solubility tests in a set of selected solvents; its powder X-ray diffraction pattern corresponds to the thermodynamically stable form as published in the IPCOM publication 000211139D of Sep. 22, 2011 and CN-A-102336801 (form I).

Aqueous solubility: 2 ml of purified water (Fluka 95304) or 2 ml 0.5M aqueous solution of organic acid (in the case of ascorbic acid: 176 mg) are added to about 30 mg of the substance to be measured. The resulting suspension is equilibrated in a temperature-controlled Eppendorf Thermomixer Comfort shaker for 2 hours or 24 hours at 25° C. at a shaking rate of 700 rpm. After 2 hours, or 24 hours, the solid phases are recovered by filter centrifugation (0.22 μm PVDF membrane). Concentrations in the filtrate after 2 hours or 24 hours (i.e. saturated solution) are determined by HPLC using under conditions given in the below Table; limit of detection (LOD) is ca. one microgram per ml. The pH of the saturated solution is determined with a Metrohm 713 pH meter.

TABLE

HPLC method used for solubility determinations.

| | |
|---|---|
| Instrument | Agilent 1100 Series with Agilent 1260 Infinity |
| Column | Waters, XTerra MS C18, 4.6 × 1000 mm, 5 μm (FK-CC01F) |
| Mobile Phase A | water, 0.1% TFA |
| Mobile Phase B | Acetonitrile |
| time 0 minutes | 95% A/5% B |
| time 20 minutes | 5% A/95% B |
| Retention time for abiraterone acetate | about 12.8 minutes |
| Flow | 1.0 mL/min |
| Injection Volume | 20 μL |
| Column Temp. | 25° C. |
| Wavelength | 236 or 248 nm |

EXAMPLE 1: Co-Crystal with Adipic Acid a) 200 mg of abiraterone acetate and 108 mg adipic acid are dissolved in 2.0 ml acetone at r.t. and 1.0 ml heptane is added. About 30% of the solvents are slowly evaporated under nitrogen at 40° C., and after about two hours about 2 ml of a turbid solution is obtained. The mixture is allowed to cool to room temperature, and after stirring for two hours a suspension obtained. The solid is filtered off and investigated by PXRD. The obtained PXRD pattern indicates the presence of a new crystalline material, but also shows peaks of the educt abiraterone acetate.

b) 195 mg of abiraterone acetate and 70 mg adipic acid are dissolved in 2.0 ml acetone at 40° C. The solution is allowed to cool to r.t. and stirred, then seeded with about 20 mg of the product obtained in the above example 1a. A thick suspension is obtained, which is stirred at r.t. for about 45 minutes. The suspension is filtered and the crystalline product dried in air at r.t. The obtained solid form is characterized by H-NMR spectroscopy, powder X-ray diffraction, TG-FTIR, and aqueous solubility measurements. H-NMR suggests a molar ratio of abiraterone acetate to adipic acid of about 2:1. The obtained PXRD pattern is shown in FIG. 1, and the corresponding peaklist is presented in Table 1. The obtained PXRD pattern neither shows presence of free adipic acid nor abiraterone acetate. TG-FTIR does not reveal any significant mass loss upon heating to 200° C. at a heating rate of 10°/min; therefore this co-crystal is neither a solvate nor a hydrate.

c) 199 mg abiraterone acetate and 107 mg adipic acid are dissolved in 2 mL acetone at room temperature. Precipitation is observed after 10 min. The suspension is stirred for further 10 min, filtered and dried at room temperature. The obtained solid form is characterized by H-NMR spectroscopy, powder X-ray diffraction, TG data, and aqueous solubility measurements. The obtained PXRD pattern complies with the pattern shown in FIG. 1. TG data does not reveal any significant mass loss upon heating to 110° C. at a heating rate of 10°/min. The first endothermal event is observed with an onset of 112° C. (96 J/g). DVS data shows that the co-crystal is not hygroscopic.

The PXRD pattern of abiraterone acetate adipic acid co-crystal 2:1 complies with the result of the single crystal structure (Table 1a). The co-crystal crystallizes in the monoclinic space group $P2_1$. The stoichiometry of the co-crystal can be proven by the crystal structure. The crystal structure also shows that no protonation/deprotonation is present. Unit cell dimensions are shown in Table 1a.

Since the pKa of adipic acid is 4.44, this new solid form may be considered as a cocrystal.

TABLE 1

PXRD: 2-theta angles, d-spacings in Å and qualitative relative intensities for the abiraterone acetate - adipic acid co-crystal

| Angle °2 θ | d-spacinq [Å] | relative intensity (qualitative) |
|---|---|---|
| 2.9 | 30.6 | vw |
| 7.6 | 11.6 | w |
| 7.9 | 11.2 | vw |
| 8.3 | 10.6 | w |
| 9.9 | 9.0 | m |
| 14.4 | 6.2 | m |
| 14.6 | 6.1 | w |
| 14.8 | 5.99 | w |
| 15.3 | 5.80 | w |
| 15.7 | 5.63 | vs |
| 16.5 | 5.38 | w |
| 16.7 | 5.30 | s |
| 18.1 | 4.90 | s |
| 18.8 | 4.71 | w |
| 19.5 | 4.54 | m |
| 19.8 | 4.47 | s |
| 20.7 | 4.28 | w |
| 21.2 | 4.20 | w |
| 21.8 | 4.07 | s |
| 23.3 | 3.81 | w |
| 23.6 | 3.77 | w |
| 24.0 | 3.71 | s |
| 24.7 | 3.60 | vw |
| 25.2 | 3.54 | m |
| 26.0 | 3.42 | w |
| 26.3 | 3.38 | m |
| 27.1 | 3.29 | w |
| 28.0 | 3.18 | m |
| 28.8 | 3.10 | m |

TABLE 1a

Crystallographic data for abiraterone acetate adipic acid co-crystal 2:1

| | |
|---|---|
| crystal system | monoclinic |
| space group | $P2_1$ |
| a (Å) | 11.5562(7) |
| b (Å) | 7.1751(4) |
| c (Å) | 30.7235(17) |
| α (°) | 90.00 |
| β (°) | 95.948(2) |
| γ (°) | 90.00 |
| V (Å$^3$) | 2533.8(3) |

TABLE 1a-continued

Crystallographic data for abiraterone
acetate adipic acid co-crystal 2:1

| | |
|---|---|
| Z | 2 |
| T (K) | 100(2) |
| $\rho_{calc}$ (g/cm$^3$) | 1.218 |
| $\lambda$ (Å) | 1.54178 |

EXAMPLE 2: Abiraterone Acetate-Citrate 6.0 ml of a mixture of acetone and n-heptane (1:1 v/v) is added to 394 mg of abiraterone acetate and 193 mg of citric acid. The mixture is heated to 60° C. and further 6.0 ml of acetone is added; the system is then allowed to cool to room temperature. After overnight stirring, the suspension is filtered and the solid dried in air at room temperature and characterized by H-NMR spectroscopy, powder X-ray diffraction, TG-FTIR, DSC, DVS and aqueous solubility measurements. H-NMR reveals a molar ratio of abiraterone acetate to citric acid of about 1:1. The obtained PXRD pattern is shown in FIG. 2 and the corresponding peaklist is presented in Table 2. TG-FTIR does not reveal any significant mass loss upon heating to 200° C. at a heating rate of 10°/min; therefore the material obtained is neither a solvate nor a hydrate. Differential scanning calorimetry shows a single melting peak at 166° C. suggesting that the molecular crystal is a single crystalline phase. Investigation by DVS shows favorable hygroscopic properties: maximum water up-take at 95% r.h. is less than 0.5%, and about 0.1 to 0.2% at 80% r.h.

Since the pKa of citric acid is 3.13, the new solid form is classified as a salt.

TABLE 2

PXRD of abiraterone acetate - citric acid salt

| Angle °2 θ | d-spacing [Å] | relative intensity (qualitative) |
|---|---|---|
| 5.0 | 17.6 | m |
| 7.7 | 11.5 | m |
| 8.1 | 10.9 | w |
| 9.9 | 8.9 | w |
| 10.3 | 8.6 | w |
| 10.9 | 8.1 | w |
| 11.2 | 7.9 | w |
| 11.7 | 7.6 | w |
| 12.5 | 7.1 | m |
| 12.9 | 6.8 | w |
| 13.2 | 6.7 | w |
| 13.8 | 6.4 | m |
| 14.4 | 6.2 | m |
| 15.5 | 5.72 | w |
| 16.0 | 5.52 | m |
| 16.2 | 5.46 | s |
| 17.0 | 5.22 | m |
| 17.2 | 5.14 | vs |
| 18.1 | 4.90 | m |
| 18.6 | 4.76 | m |
| 18.9 | 4.68 | w |
| 19.4 | 4.57 | vs |
| 20.3 | 4.37 | m |
| 20.7 | 4.29 | w |
| 21.5 | 4.13 | w |
| 22.6 | 3.93 | w |
| 22.8 | 3.89 | w |
| 23.8 | 3.74 | w |
| 24.5 | 3.62 | w |
| 24.9 | 3.57 | w |

TABLE 2-continued

PXRD of abiraterone acetate - citric acid salt

| Angle °2 θ | d-spacing [Å] | relative intensity (qualitative) |
|---|---|---|
| 25.9 | 3.44 | s |
| 26.5 | 3.36 | m |

EXAMPLE 3: Abiraterone Acetate-D,L-Malate a) 394 mg abiraterone acetate and 135 mg of D,L-malic acid are dissolved in 2.0 ml acetonitrile by heating to 60° C. The solution is allowed to cool to room temperature and stirred for several hours. The solvent is slowly evaporated under a slight flow of nitrogen of about 10 ml per minute. After complete evaporation of the solvent, a crystalline sample is obtained which is characterized by H-NMR spectroscopy, powder X-ray diffraction, and aqueous solubility measurements. H-NMR reveals a molar ratio of abiraterone acetate to malic acid of about 1:1. The powder X-ray diffraction pattern which is depicted in FIG. 3 shows a clearly crystalline sample that does not indicate the presence of the abiraterone acetate educt. DVS shows a maximum water up-take at 95% r.h. of less than 4%.

b) 402 mg abiraterone acetate and 132 mg of D,L-malic acid are dissolved in 2.0 ml acetonitrile by heating to 60° C. The solvent is evaporated by rotary evaporation, redissolved in 1 mL acetonitrile and 1 mL heptane and stirred for 3 d. The suspension is filtered and dried at room temperature. The powder X-ray diffraction pattern complies with the pattern in FIG. 3. TG data show no significant mass loss up to 130° C. Decomposition starts above 150° C. The DSC trace shows two endothermal events. The first event is observed with an onset of 99° C. (78 J/g). The second endothermal event (onset 179° C., 111 J/g) correlates with the mass loss of approx. 25%.

Since the pKa of malic acid is 3.5, the new solid form is classified as a salt.

TABLE 3

PXRD of abiraterone acetate - D,L-malate salt

| Angle °2 θ | d-spacing [Å] | relative intensity (qualitative) |
|---|---|---|
| 4.4 | 20.2 | m |
| 7.8 | 11.3 | w |
| 8.1 | 10.9 | w |
| 8.6 | 10.2 | m |
| 8.9 | 9.9 | vw |
| 10.2 | 8.7 | w |
| 11.7 | 7.6 | w |
| 13.3 | 6.6 | m |
| 15.3 | 5.80 | w |
| 15.7 | 5.65 | w |
| 16.0 | 5.53 | w |
| 16.2 | 5.46 | m |
| 16.5 | 5.37 | m |
| 17.0 | 5.23 | vs |
| 17.3 | 5.11 | m |
| 17.6 | 5.03 | m |
| 17.9 | 4.95 | m |
| 18.5 | 4.78 | w |
| 18.9 | 4.68 | m |
| 19.6 | 4.53 | m |
| 21.3 | 4.17 | m |
| 21.6 | 4.10 | m |
| 22.7 | 3.91 | w |
| 23.8 | 3.74 | w |
| 24.2 | 3.67 | w |

TABLE 3-continued

PXRD of abiraterone acetate - D,L-malate salt

| Angle °2 θ | d-spacing [Å] | relative intensity (qualitative) |
|---|---|---|
| 24.4 | 3.64 | m |
| 28.1 | 3.17 | w |

EXAMPLE 4: Abiraterone Acetate-Maleic Acid a) Example for the Preparation of Abiraterone Acetate-Maleate Form A.

To about 40 mg abiraterone acetate-maleate form B (see example 4b) and about 40 mg abiraterone acetate-maleate form C (see example 4c) is added 2.0 ml acetonitrile and about 20 microliter of water. The obtained suspension is stirred at room temperature for about 16 hours, then the solid is separated off by centrifugal filtration and investigated by powder X-ray diffraction. A PXRD pattern as shown in FIG. 4a with peak locations as provided in Table 4a is obtained. The powder X-ray diffraction pattern shows a clearly crystalline sample that does not indicate the presence of a significant amount of abiraterone acetate form I.

b) Example for the Preparation of Abiraterone Acetate-Maleate Form B.

395 mg abiraterone acetate and 117 mg maleic acid are dissolved in 3.8 ml acetonitrile at 60° C. The hot solution is allowed to cool to room temperature and then stirred overnight before the solid product is separated by filtration and dried in air at r.t. Characterization by H-NMR spectroscopy indicates a molar ratio of abiraterone acetate to maleic acid of about 1:1. Powder X-ray diffraction shows a pattern as depicted in FIG. 4b with peak locations as provided in Table 4b. Differential scanning calorimetry of form B shows a single sharp melting peak at 141° C. Further characterization TG-FTIR suggests that the crystalline material is neither a solvate nor a hydrate; TG-FTIR of abiraterone acetate-maleate form B reveals a small mass loss of less than about 0.1% upon heating to 120° C. at a rate of 10 K/min. Thermal decomposition begins at about 140° C., concurrent with the melting process.

c) Example for the Preparation of Abiraterone Acetate-Maleate Form C.

To 79 mg abiraterone acetate form I and 24 mg maleic acid is added 100 μl acetonitrite. This mixture is vigorously ground in an agate mortar. Solvent addition of 100 μl acetone and grinding is repeated with the same mixture until the solvent is evaporated. The solid is investigated by PXRD; a PXRD pattern as shown in FIG. 4c with peak locations as provided in Table 4c is obtained. The powder X-ray diffraction pattern shows a clearly crystalline sample that does not indicate the presence of a significant amount of abiraterone acetate form I.

d) Example for the Preparation of Abiraterone Acetate-Maleate Form D.

391 mg abiraterone acetate and 114 mg maleic acid are dissolved in 3.8 ml acetonitrile at 60° C. The hot solution is allowed to cool to room temperature and then stirred overnight. The solvent is evaporated (35° C., 60 mbar) and an amorphous solid is obtained, which subsequently is suspended in 1 mL of acetonitrile and stirred for 3 days. The solid is filtered and dried. Powder X-ray diffraction shows a pattern as depicted in FIG. 4d with peak locations as provided in Table 4d. Differential scanning calorimetry of form D shows a single sharp melting peak at 120° C. TG data suggests that the crystalline material is neither a solvate nor a hydrate; TG of abiraterone acetate-maleate form D reveals a small mass loss of less than about 0.1% upon heating to 120° C. at a rate of 10 K/min. Thermal decomposition begins at about 130° C.

The pKa of maleic acid being 1.9, the new crystalline solid forms obtained with maleic acid are rather salts than co-crystals, because the pKa difference is greater than 1.0.

TABLE 4a

PXRD peaktable of abiraterone acetate - maleate form A salt

| Angle °2 θ | d-spacing [Å] | relative intensity (qualitative) |
|---|---|---|
| 6.4 | 13.7 | w |
| 8.7 | 10.2 | w |
| 11.4 | 7.7 | m |
| 12.8 | 6.9 | vw |
| 13.4 | 6.6 | vs |
| 14.5 | 6.1 | s |
| 15.6 | 5.69 | w |
| 16.6 | 5.33 | w |
| 17.0 | 5.23 | w |
| 17.3 | 5.14 | m |
| 17.6 | 5.03 | vs |
| 18.2 | 4.87 | w |
| 18.5 | 4.78 | w |
| 19.1 | 4.64 | w |
| 19.9 | 4.46 | m |
| 20.8 | 4.26 | m |
| 21.7 | 4.09 | w |
| 21.9 | 4.05 | w |
| 22.2 | 4.00 | w |
| 22.7 | 3.92 | w |
| 22.9 | 3.88 | m |
| 23.4 | 3.80 | w |
| 24.1 | 3.69 | m |
| 24.9 | 3.57 | w |
| 25.5 | 3.49 | w |
| 25.9 | 3.44 | w |
| 26.4 | 3.37 | w |
| 27.7 | 3.22 | w |
| 28.1 | 3.17 | w |
| 28.7 | 3.11 | w |
| 29.5 | 3.02 | w |
| 30.8 | 2.90 | w |
| 31.2 | 2.86 | w |

TABLE 4b

PXRD peaktable of abiraterone acetate - maleate form B salt

| Angle °2 θ | d-spacing [Å] | relative intensity (qualitative) |
|---|---|---|
| 6.3 | 14.1 | w |
| 8.5 | 10.4 | w |
| 11.3 | 7.8 | m |
| 12.6 | 7.0 | w |
| 13.3 | 6.7 | s |
| 14.3 | 6.2 | s |
| 14.8 | 5.97 | w |
| 15.4 | 5.74 | m |
| 16.4 | 5.39 | w |
| 16.8 | 5.27 | s |
| 17.1 | 5.19 | m |
| 17.4 | 5.08 | vs |
| 17.6 | 5.04 | s |
| 18.0 | 4.91 | w |
| 18.4 | 4.82 | s |
| 18.9 | 4.68 | w |
| 19.7 | 4.51 | s |
| 20.6 | 4.30 | s |
| 20.9 | 4.25 | w |
| 21.5 | 4.13 | m |
| 21.7 | 4.09 | m |

TABLE 4b-continued

PXRD peaktable of abiraterone acetate - maleate form B salt

| Angle °2 θ | d-spacing [Å] | relative intensity (qualitative) |
|---|---|---|
| 22.1 | 4.02 | w |
| 22.7 | 3.91 | s |
| 23.2 | 3.83 | m |
| 23.8 | 3.74 | m |
| 23.9 | 3.72 | m |
| 24.7 | 3.60 | m |
| 25.3 | 3.51 | s |
| 25.5 | 3.48 | m |
| 26.3 | 3.39 | s |
| 27.1 | 3.29 | w |
| 27.6 | 3.23 | m |
| 27.9 | 3.19 | s |

TABLE 4c

PXRD peaktable of abiraterone acetate - maleate form C salt

| Angle °2 θ | d-spacing [Å] | relative intensity (qualitative) |
|---|---|---|
| 3.7 | 24.0 | vw |
| 4.3 | 20.8 | vw |
| 5.9 | 14.9 | vw |
| 7.8 | 11.3 | w |
| 8.2 | 10.8 | vs |
| 8.4 | 10.5 | m |
| 8.9 | 9.9 | m |
| 9.6 | 9.2 | vw |
| 10.1 | 8.7 | s |
| 10.6 | 8.4 | w |
| 12.0 | 7.3 | w |
| 14.0 | 6.3 | w |
| 14.5 | 6.1 | w |
| 14.9 | 5.94 | w |
| 15.2 | 5.81 | w |
| 15.8 | 5.61 | s |
| 15.9 | 5.55 | m |
| 16.1 | 5.50 | m |
| 16.3 | 5.42 | s |
| 16.5 | 5.36 | m |
| 17.0 | 5.21 | vs |
| 17.3 | 5.12 | m |
| 17.9 | 4.95 | s |
| 19.2 | 4.62 | w |
| 18.6 | 4.76 | w |
| 20.3 | 4.38 | s |
| 21.2 | 4.20 | w |
| 21.5 | 4.14 | w |
| 21.9 | 4.06 | m |
| 22.0 | 4.04 | m |
| 22.7 | 3.91 | m |
| 23.3 | 3.82 | m |
| 23.6 | 3.77 | s |
| 23.8 | 3.73 | m |
| 24.6 | 3.62 | m |
| 24.8 | 3.58 | w |
| 25.3 | 3.52 | m |

TABLE 4d

PXRD peaktable of abiraterone acetate - maleate form D salt

| Angle °2 θ | d-spacing [Å] | relative intensity (qualitative) |
|---|---|---|
| 5.2 | 17.2 | w |
| 8.4 | 10.5 | w |
| 10.3 | 8.6 | vw |
| 10.6 | 8.3 | w |
| 11.3 | 7.8 | vw |
| 12.2 | 7.3 | vw |
| 13.3 | 6.7 | m |
| 13.9 | 6.4 | wv |
| 14.3 | 6.2 | w |
| 14.8 | 6.0 | vs |
| 15.1 | 5.88 | w |
| 15.3 | 5.78 | m |
| 15.5 | 5.71 | m |
| 15.9 | 5.57 | w |
| 16.6 | 5.36 | s |
| 16.8 | 5.27 | w |
| 17.2 | 5.17 | m |
| 17.5 | 5.08 | s |
| 18.4 | 4.82 | w |
| 19.4 | 4.58 | s |
| 20.9 | 4.26 | m |
| 21.3 | 4.17 | s |
| 23.4 | 3.81 | w |
| 23.6 | 3.77 | w |
| 24.8 | 3.59 | w |
| 26.6 | 3.36 | w |
| 27.0 | 3.31 | vw |
| 27.7 | 3.23 | w |
| 28.0 | 3.19 | vw |

EXAMPLE 5: Co-Crystal with Methyl-4-Hydroxy Benzoate a) 264 mg abiraterone acetate and 101 mg methyl-4-hydroxy benzoate are dissolved in a mixture of 2.0 ml ethyl acetate and 4.0 ml heptane, then is added 3.0 ml heptane and the mixture is stirred at r.t. while keeping the vial open to let some solvent evaporate. After overnight stirring a suspension is obtained, the cap of the vial is closed and stirring is continued for about one hour. After filtration the solid is dried in air at room temperature for about one hour and characterized by PXRD, TG-FTIR, DSC, H-NMR, and solubility tests aqueous media. H-NMR spectroscopy shows about a 1:1 ratio of abiraterone acetate to methyl-4-hydroxy benzoate. TG-FTIR reveals a small mass loss of about 0.4% upon heating to 150° C. at a rate of 10 K/min. Thermal decomposition begins between 170 and 180° C. Differential scanning calorimetry shows a single sharp melting peak at 101° C. with an enthalpy of fusion of about 74 J/g (melting peak clearly lower than the melting temperature of methyl-4-hydroxy benzoate and abiraterone acetate). A PXRD pattern as shown in FIG. 5a with peak locations as provided in Table 5a (form A) is obtained. Investigation of the abiraterone acetate methyl-4-hydroxy benzoate co-crystal by DVS shows that this solid form exhibits favorable hygroscopic properties as the maximum water up-take at 95% r.h. is less than 0.4% and about 0.2% at 80% r.h.

b) 398 mg abiraterone acetate and 154 mg methyl-4-hydroxy benzoate are dissolved in 10.0 ml heptane-ethyl acetate 2:1 at 60° C. The obtained solution is allowed to cool to room temperature and stirred for about 16 hours (overnight) before the formed crystalline material is separated by filtration and dried under vacuum for four hours at room temperature. H-NMR spectroscopy indicates a molar ratio of abiraterone acetate to methyl-4-hydroxy benzoate of about 1:1. A PXRD pattern as shown in FIG. 5a with peak locations as provided in Table 5a (form A) is obtained.

c) To 80 mg abiraterone acetate and 31 mg methyl-4-hydroxy benzoate is added 50 microliter ethyl acetate, and this mixture is vigorously ground in an agate mortar at least for five minutes or until the solvent is evaporated. Solvent addition of another 50 microliter ethyl acetate and grinding is repeated twice with the same mixture; then PXRD is performed. The PXRD pattern obtained is the one of form A (same as in examples (a) and (b)).

d) 534 mg abiraterone acetate methyl-4-hydroxy benzoate co-crystal are suspended at 40° C. in 5 mL heptane/EtOAc (9/1) for 1 h, cooled to room temperature, stirred at room temperature for 8 h. 3 mL heptane are added, the suspension is stirred for 1 h, filtered and dried at room temperature. A PXRD pattern as shown in FIG. 5b with peak locations as provided in Table 5b (form B) is obtained.

e) 534 mg abiraterone acetate methyl-4-hydroxy benzoate co-crystal are suspended at 40° C. in 5 mL heptane/EtOAc (9/1) for 1 h, cooled to room temperature, stirred at room temperature for 8 h. 3 mL heptane are added, the suspension is stirred for 1 h, filtered and dried at room temperature in vacuum for 2.5 h. H-NMR spectroscopy shows about a 1:1 ratio of abiraterone acetate to methyl-4-hydroxy benzoate. TG data reveals a small mass loss of about 0.1% upon heating to 100° C. at a rate of 10 K/min. Thermal decomposition begins at about 150° C. Differential scanning calorimetry shows a single sharp melting peak at 100° C. with an enthalpy of fusion of about 83 J/g. The PXRD pattern complies with the pattern shown in FIG. 5a (form A). Investigation of the abiraterone acetate methyl-4-hydroxy benzoate co-crystal by DVS shows that this solid form exhibits favorable hygroscopic properties as the maximum water up-take at 95% r.h. is less than 0.4% and about 0.2% at 80% r.h.

f) 40 mg abiraterone acetate and 15 mg methyl-4-hydroxy benzoate are dissolved in 2.5 mL n-heptane/ethyl acetate (2:1) at 60° C. The suspension is cooled to room temperature and solvents are allowed to slowly evaporate. Needle-like crystals are obtained. The single crystal structure shows the abiraterone acetate/methyl-4-hydroxy benzoate 1:1 co-crystal form C. The co-crystal crystallizes in the monoclinic space group P21. The crystal structure also shows that no protonation/deprotonation is observed. Unit cell dimensions as determined at 100 K are shown in Table 5c, numbers in brackets indicate the error margin in the last digit. Powder x-ray diffraction peaks (d-values in Angstroem or 2 thetha-values under the condition of Cu k-alpha radiation) calculated from these single crystal data are given in Table 5d and FIG. 5c (Mercury CSD 3.3, Cambridge Crystallographic Data Centre). Crystallographic data of form C are clearly distinguished from those of abiraterone acetate/methyl-4-hydroxy benzoate co-crystal forms A and B.

TABLE 5a

PXRD peaktable of abiraterone acetate/methyl-4-hydroxy benzoate co-crystal form A

| Angle °2 θ | d-spacing [Å] | relative intensity (qualitative) |
|---|---|---|
| 8.3 | 10.7 | w |
| 8.9 | 9.9 | vw |
| 9.6 | 9.2 | s |
| 11.4 | 7.8 | w |
| 13.9 | 6.4 | w |
| 14.7 | 6.0 | vw |
| 15.2 | 5.84 | vw |
| 16.8 | 5.26 | w |
| 17.2 | 5.15 | m |
| 17.5 | 5.05 | w |
| 18.0 | 4.93 | s |
| 18.3 | 4.84 | vs |
| 18.6 | 4.78 | w |
| 20.2 | 4.38 | m |
| 20.8 | 4.26 | w |
| 22.6 | 3.93 | w |
| 22.8 | 3.89 | m |
| 24.3 | 3.65 | w |
| 25.2 | 3.53 | w |
| 27.1 | 3.28 | m |
| 28.0 | 3.18 | w |
| 29.1 | 3.06 | w |

TABLE 5b

PXRD peaktable of abiraterone acetate/methyl-4-hydroxy benzoate co-crystal form B

| Angle °2 θ | d-spacing [Å] | relative intensity (qualitative) |
|---|---|---|
| 17.3 | 5.13 | w |
| 17.7 | 5.02 | m |
| 18.0 | 4.93 | w |
| 18.5 | 4.80 | s |
| 18.8 | 4.72 | vs |
| 20.7 | 4.29 | s |
| 21.3 | 4.17 | m |
| 23.3 | 3.81 | s |
| 24.8 | 3.59 | m |
| 25.7 | 3.47 | m |
| 26.6 | 3.35 | w |
| 27.6 | 3.23 | s |
| 28.6 | 3.12 | w |
| 29.6 | 3.02 | m |
| 31.2 | 2.87 | w |
| 31.7 | 2.82 | w |
| 32.4 | 2.77 | w |
| 33.3 | 2.69 | w |

TABLE 5c

Crystallographic data for abiraterone acetate methyl-4-hydroxy benzoate 1:1 form C (T = 100 K)

| | |
|---|---|
| crystal system | monoclinic |
| space group | P2$_1$ |
| a (Å) | 14.5515(4) |
| b (Å) | 6.2923(2) |
| c (Å) | 16.2966(4) |
| α (°) | 90.00 |
| β (°) | 101.9020(10) |
| γ (°) | 90.00 |
| V (Å$^3$) | 1460.08(7) |
| Z | 2 |
| ρ$_{calc}$ (g/cm$^3$) | 1.237 |
| λ (Å) | 1.54178 |

TABLE 5d

Calculated PXRD peaktable of abiraterone acetate/methyl-4-hydroxy benzoate co-crystal form C at a temperature of 100 K

| Angle °2 θ | d-spacing [Å] | relative intensity (qualitative) |
|---|---|---|
| 6.2 | 14.2 | m |
| 7.4 | 11.9 | vw |

TABLE 5d-continued

Calculated PXRD peaktable of abiraterone acetate/methyl-4-hydroxy benzoate co-crystal form C at a temperature of 100 K

| Angle °2 θ | d-spacing [Å] | relative intensity (qualitative) |
|---|---|---|
| 9.1 | 9.7 | w |
| 11.1 | 8.0 | w |
| 11.5 | 7.7 | w |
| 15.1 | 5.85 | s |
| 15.4 | 5.76 | s |
| 15.9 | 5.56 | m |
| 16.8 | 5.27 | s |
| 17.9 | 4.94 | m |
| 18.3 | 4.84 | m |
| 19.7 | 4.49 | w |
| 20.3 | 4.36 | vs |
| 20.6 | 4.31 | m |
| 21.9 | 4.06 | w |
| 22.3 | 3.99 | w |
| 22.8 | 3.89 | vw |
| 23.2 | 3.83 | m |
| 23.7 | 3.75 | m |
| 25.0 | 3.56 | w |
| 26.1 | 3.41 | w |
| 26.4 | 3.37 | w |
| 26.7 | 3.33 | w |
| 27.7 | 3.22 | m |
| 28.3 | 3.15 | w |
| 28.9 | 3.09 | w |
| 29.8 | 2.99 | m |

EXAMPLE 6: Abiraterone Acetate-Saccharinate a) Since the pKa of saccharin is 1.6 the new solid form is rather a salt than a co-crystal. 394 mg abiraterone acetate and 183 mg saccharin are dissolved in 5.0 ml acetonitrile-isopropanol (1:1 v/v) at 60° C. The hot solution is allowed to cool to room temperature and then stirred overnight before the solid product is separated by filtration and dried in air at r.t. The solid material is further characterized by powder X-ray diffraction, TG-FTIR, DSC, DVS and aqueous solubility measurements. H-NMR spectroscopy indicates a molar ratio of abiraterone acetate to saccharin of about 1:1. The powder X-ray diffraction pattern which is depicted in FIG. 6 shows a clearly crystalline sample with a new PXRD pattern neither showing traces of saccharin nor of abiraterone acetate. A list with peak locations is provided in Table 6. Further analysis by TG-FTIR does not reveal any significant mass loss and therefore the solid is neither a hydrate nor a solvate (small mass loss of less than 0.1% upon heating to 200° C. at a rate of 10 K/min). Thermal decomposition begins between 210 and 230° C. Differential scanning calorimetry shows a single sharp melting peak at 167° C. with an enthalpy of fusion of about 93 J/g. DVS shows favorable hygroscopic properties as the maximum water up-take at 95% r.h. is less than 0.4% and about 0.1 to 0.2% at 80% r.h.

b) 407 mg abiraterone acetate and 185 mg saccharin are dissolved in 5.0 ml acetonitrile-isopropanol (1:1 v/v) at 60° C. The hot solution is allowed to cool to room temperature and then stirred overnight, cooled to 4° C. and stored at 4° C. for 1 d. The solvent is evaporated by rotary evaporation. The white precipitate is dried in vacuum. The powder X-ray diffraction pattern complies with the pattern depicted in FIG. 6. TG analysis shows no significant mass loss up to 120° C. Decomposition starts above 200° C. Differential scanning calorimetry shows a single sharp melting peak at 163° C. with an enthalpy of fusion of about 87 J/g.

TABLE 6

PXRD peaktable of abiraterone acetate - saccharin salt

| Angle °2 θ | d-spacing [Å] | relative intensity (qualitative) |
|---|---|---|
| 6.6 | 13.5 | w |
| 8.9 | 10.0 | m |
| 11.5 | 7.7 | w |
| 11.9 | 7.4 | w |
| 12.2 | 7.2 | w |
| 12.4 | 7.1 | vw |
| 13.2 | 6.7 | vs |
| 13.5 | 6.5 | s |
| 13.7 | 6.5 | m |
| 14.5 | 6.1 | w |
| 14.8 | 5.99 | s |
| 15.4 | 5.74 | m |
| 16.5 | 5.36 | s |
| 17.1 | 5.17 | w |
| 17.5 | 5.05 | s |
| 17.8 | 4.99 | w |
| 18.1 | 4.90 | w |
| 18.7 | 4.74 | m |
| 19.1 | 4.63 | w |
| 19.5 | 4.54 | w |
| 19.8 | 4.48 | w |
| 20.4 | 4.35 | s |
| 20.7 | 4.28 | vs |
| 20.9 | 4.25 | w |
| 21.2 | 4.19 | w |
| 21.4 | 4.14 | m |
| 21.8 | 4.08 | w |
| 22.5 | 3.94 | m |
| 23.2 | 3.84 | w |
| 23.6 | 3.76 | w |
| 23.8 | 3.74 | w |
| 23.9 | 3.72 | s |
| 24.3 | 3.67 | w |
| 24.5 | 3.63 | w |
| 24.7 | 3.60 | w |
| 25.4 | 3.51 | w |
| 26.1 | 3.41 | s |

EXAMPLE 7: Abiraterone Acetate-L-Tartrate Forms

WO 2006/021776 describes one salt of abiraterone acetate with tartaric acid without further characterization. Performing the experiment described in WO 2006/021776 yields the crystalline form described herein as abiraterone acetate-L-tartrate form A (see below example 7a).

The crystalline solid forms obtained with L-tartaric acid are salts rather than co-crystals, because the pKa difference is greater than 1.0.

a) Example for the Preparation of Abiraterone Acetate-L-Tartrate Form A:

To 79 mg abiraterone acetate and 30 mg L-tartaric acid is added 100 microliter acetone, and this mixture is vigorously ground in an agate mortar at least for five minutes. Solvent addition of 100 microliter acetone and grinding is repeated twice with the same mixture before PXRD is performed. A PXRD pattern as shown in FIG. 7a with peak locations as provided in Table 7a is obtained. H-NMR spectroscopy reveals a molar ratio of abiraterone acetate to L-tartaric acid of about 1:1.

b) Example for the Preparation of Abiraterone Acetate-L-Tartrate Form B:

To 160 mg abiraterone acetate and 60 mg L-tartaric acid is added 15.0 ml acetonitrile and 2.0 ml acetone. This mixture is heated to 60° C. and stirred at this temperature for 8 hours, then the heater is turned off and stirring is continued overnight; on the next day the obtained suspension is filtered and the solid dried in air at room temperature. A PXRD pattern as shown in FIG. 7b with peak locations as provided in Table 7b is obtained. H-NMR spectroscopy reveals a molar ratio of abiraterone acetate to L-tartaric acid of about 1:1.

c) Example for the Preparation of Abiraterone Acetate-L-Tartrate Form C:

About 25 mg of the abiraterone acetate-L-tartrate form B according to the previous example are subjected to a variable relative humidity program in a dynamic vapor sorption instrument type SPS11-100n. Powder X-ray diffraction of the sample recovered from the DVS sample pan after the measurement results in a PXRD pattern as depicted in FIG. 7c with peak locations as listed in Table 7c.

TABLE 7a

PXRD peaktable of abiraterone acetate - L-tartrate form A

| Angle °2 θ | d-spacing [Å] | relative intensity (qualitative) |
|---|---|---|
| 4.9 | 18.0 | m |
| 9.8 | 9.1 | w |
| 9.9 | 8.9 | w |
| 11.8 | 7.5 | vw |
| 12.1 | 7.3 | w |
| 13.1 | 6.8 | w |
| 14.6 | 6.1 | m |
| 14.9 | 5.94 | w |
| 15.1 | 5.85 | m |
| 15.7 | 5.63 | s |
| 16.0 | 5.53 | w |
| 17.0 | 5.21 | m |
| 17.3 | 5.12 | vs |
| 18.1 | 4.89 | vs |
| 18.5 | 4.80 | w |
| 19.0 | 4.67 | w |
| 19.2 | 4.63 | w |
| 19.5 | 4.54 | w |
| 20.0 | 4.43 | m |
| 20.8 | 4.28 | m |
| 21.0 | 4.23 | w |
| 21.4 | 4.15 | s |
| 21.8 | 4.08 | m |
| 22.0 | 4.04 | w |
| 22.5 | 3.94 | w |
| 22.7 | 3.91 | w |
| 23.1 | 3.84 | w |
| 23.6 | 3.77 | s |
| 25.1 | 3.55 | w |
| 25.3 | 3.52 | w |
| 26.1 | 3.41 | w |
| 26.4 | 3.37 | w |
| 27.9 | 3.20 | w |
| 28.1 | 3.17 | m |

TABLE 7b

PXRD peaktable of abiraterone acetate - L-tartrate form B

| Angle °2 θ | d-spacing [Å] | relative intensity (qualitative) |
|---|---|---|
| 5.2 | 17.0 | s |
| 7.9 | 11.2 | vs |
| 10.3 | 8.6 | m |
| 11.0 | 8.0 | w |
| 12.3 | 7.2 | w |
| 12.9 | 6.8 | m |
| 14.6 | 6.1 | s |
| 15.2 | 5.84 | s |
| 15.4 | 5.75 | w |
| 15.8 | 5.59 | vs |
| 16.1 | 5.49 | s |
| 16.3 | 5.43 | s |
| 16.8 | 5.28 | w |
| 17.3 | 5.11 | w |
| 17.6 | 5.04 | w |
| 18.1 | 4.91 | w |
| 18.5 | 4.78 | m |
| 19.1 | 4.65 | w |
| 20.1 | 4.41 | m |
| 20.4 | 4.36 | w |
| 20.7 | 4.29 | w |
| 20.9 | 4.25 | m |
| 21.0 | 4.22 | w |
| 21.7 | 4.09 | w |
| 22.0 | 4.05 | vs |
| 22.3 | 3.98 | s |
| 23.3 | 3.81 | w |
| 24.0 | 3.71 | w |
| 24.1 | 3.68 | w |
| 24.8 | 3.59 | m |
| 25.2 | 3.54 | w |
| 25.7 | 3.46 | w |
| 26.2 | 3.40 | w |
| 26.4 | 3.37 | w |
| 26.8 | 3.32 | m |

TABLE 7c

PXRD peaktable of abiraterone acetate - L-tartrate form C

| Angle °2 θ | d-spacing [Å] | relative intensity (qualitative) |
|---|---|---|
| 4.2 | 21.1 | s |
| 4.9 | 18.1 | w |
| 5.2 | 16.9 | w |
| 6.1 | 14.5 | w |
| 7.9 | 11.1 | m |
| 8.4 | 10.6 | s |
| 8.8 | 10.0 | s |
| 9.8 | 9.1 | w |
| 10.6 | 8.3 | m |
| 11.5 | 7.7 | w |
| 12.0 | 7.4 | m |
| 12.3 | 7.2 | w |
| 13.0 | 6.8 | w |
| 13.5 | 6.5 | s |
| 13.9 | 6.4 | m |
| 14.6 | 6.0 | m |
| 15.1 | 5.87 | m |
| 15.7 | 5.64 | m |
| 15.9 | 5.58 | m |
| 16.2 | 5.47 | s |
| 16.7 | 5.29 | vs |
| 17.0 | 5.22 | s |
| 17.3 | 5.11 | vs |
| 17.7 | 5.01 | vs |
| 18.1 | 4.89 | s |
| 18.3 | 4.83 | s |
| 19.2 | 4.63 | s |
| 20.1 | 4.42 | s |
| 20.5 | 4.33 | s |
| 20.9 | 4.24 | m |
| 21.4 | 4.16 | m |
| 22.0 | 4.04 | s |
| 22.4 | 3.964 | m |
| 23.4 | 3.81 | s |
| 23.6 | 3.77 | s |
| 24.1 | 3.69 | m |
| 24.4 | 3.64 | m |
| 25.1 | 3.54 | s |
| 25.4 | 3.50 | m |
| 26.0 | 3.43 | m |

EXAMPLE 8: Cocrystal of Abiraterone Acetate and Vanillic Acid

Since the pKa of vanillic acid is 4.45, the new crystalline solid is classified as a cocrystal.

a) 197 mg abiraterone acetate and 86 mg of vanillic acid (Fluka #94770) are dissolved in 2.0 ml isopropanol by heating to 60° C. The solution is stirred at r.t. until a suspension is obtained. The obtained thick suspension is diluted with 1.0 ml isopropanol, and stirring is continued for two hours before the solid is separated by filtration. After drying in air at room temperature, the crystalline product is characterized by PXRD and H-NMR spectroscopy. H-NMR indicates a molar ratio of abiraterone acetate to vanillic acid of about 1:1. The powder X-ray diffraction pattern as depicted in FIG. 8 shows a clearly crystalline sample that does neither indicate the presence abiraterone acetate form I nor vanillic acid at a significant level. The peak locations are provided in Table 8.

b) 795 mg abiraterone acetate and 345 mg of vanillic acid are dissolved at room temperature in 8 mL of isopropanol. The solution is stirred for 8 h in an open vial. Crystallization is observed, and remaining solvent is evaporated in a nitrogen stream. 1H-NMR indicates a molar ratio of abiraterone acetate to vanillic acid of about 1:1. The powder X-ray diffraction pattern complies with the pattern shown in FIG. 8. TG data reveals a small mass loss of about 0.5% upon heating to 125° C. at a rate of 10 K/min. Thermal decomposition begins between 170 and 180° C. Differential scanning calorimetry shows a single sharp melting peak at 127° C. with an enthalpy of fusion of about 50 J/g. Investigation of the abiraterone acetate vanillic acid co-crystal by DVS shows that this solid form exhibits favorable hygroscopic properties as the maximum water up-take at 95% r.h. is less than 0.4% and about 0.2% at 80% r.h.

TABLE 8

PXRD peaktable of abiraterone acetate - vanillic acid cocrystal

| Angle °2 θ | d-spacing [Å] | relative intensity (qualitative) |
|---|---|---|
| 6.0 | 14.6 | vw |
| 6.5 | 13.5 | w |
| 8.3 | 10.7 | vw |
| 11.9 | 7.4 | vw |
| 12.1 | 7.3 | vw |
| 13.1 | 6.8 | m |
| 13.3 | 6.7 | w |
| 13.9 | 6.4 | m |
| 15.1 | 5.87 | w |
| 15.5 | 5.73 | w |
| 17.2 | 5.14 | w |
| 18.2 | 4.87 | m |
| 19.3 | 4.60 | m |
| 19.7 | 4.51 | vs |
| 21.4 | 4.15 | vs |
| 22.8 | 3.90 | w |
| 23.6 | 3.76 | w |
| 24.1 | 3.70 | w |
| 24.3 | 3.66 | m |
| 24.6 | 3.62 | m |
| 24.7 | 3.60 | w |
| 25.3 | 3.51 | vw |
| 26.3 | 3.39 | w |
| 27.3 | 3.26 | w |
| 27.9 | 3.20 | s |

EXAMPLE 9: Aqueous Solubility

The aqueous solubility of co-crystals and salts of the invention is determined and compared to the aqueous solubility of abiraterone acetate. All solubility tests are conducted at 25° C. For the results in Table a), the medium is purified water. For the results in Table b), the medium is 0.5 molar aqueous ascorbic acid solution; crystallization tests show that ascorbic acid does not form a cocrystal or salt with abiraterone acetate. Results of solubility experiments are compiled in the following Tables a), b) and c). All solubility values correspond to the effective solubility of abiraterone acetate; i.e., the values are corrected for the different formula mass of the co-crystals and salts.

TABLE a

Aqueous solubility of Abiraterone acetate (comparison) and of multi-component molecular cocrystals of arbiraterone acetate with organic acid, and pH, after 24 h equilibration time.

| Coformer (pKa) | Example | S [microgram/ml] | pH |
|---|---|---|---|
| none (comparison) | — | <LOD | 8.6 |
| Citric acid (3.13) | 2 | 6.5 | 2.5 |
| D,L-Malic acid (3.5) | 3 | 13.8 | 2.2 |
| Maleic acid (1.9) | 4 | 14.4 | 2.3 |

TABLE b

Solubility of Abiraterone acetate and of multicomponent molecular co-crystals of arbiraterone acetate with organic acid, and pH, after 2 h equilibration time; medium is 0.5 molar aqueous ascorbic acid solution.

| Coformer (pKa) | Example | pH | S [microgram/ml] |
|---|---|---|---|
| Adipic acid (4.44) | 1 | 2.2 | 45.1 |
| Citric acid (3.13) | 2 | 2.1 | 63.4 |
| D,L-Malic acid (3.5) | 3 | | |
| Maleic acid (1.9) | 4 | | |
| Methyl-4-hydroxybenzoate (4.47) | 5 | 2.2 | 49.9 |
| Saccharin (1.6) | 6 | | |
| L-Tartaric acid (2.95) | 7 | | |
| Vanillic acid (4.45) | 8 | 2.2 | 48.8 |

TABLE c

Solubility of Abiraterone acetate in phosphate buffer and various amounts of organic acids

| acid | mol/L | pH | S [μg/mL] |
|---|---|---|---|
| none | — | 3.1 | 2 |
| ascorbic acid | 0.1 | 2.8 | 5 |
| ascorbic acid | 0.5 | 2.4 | 33 |
| citric acid | 0.5 | 2.3 | 14 |

Figure 1:
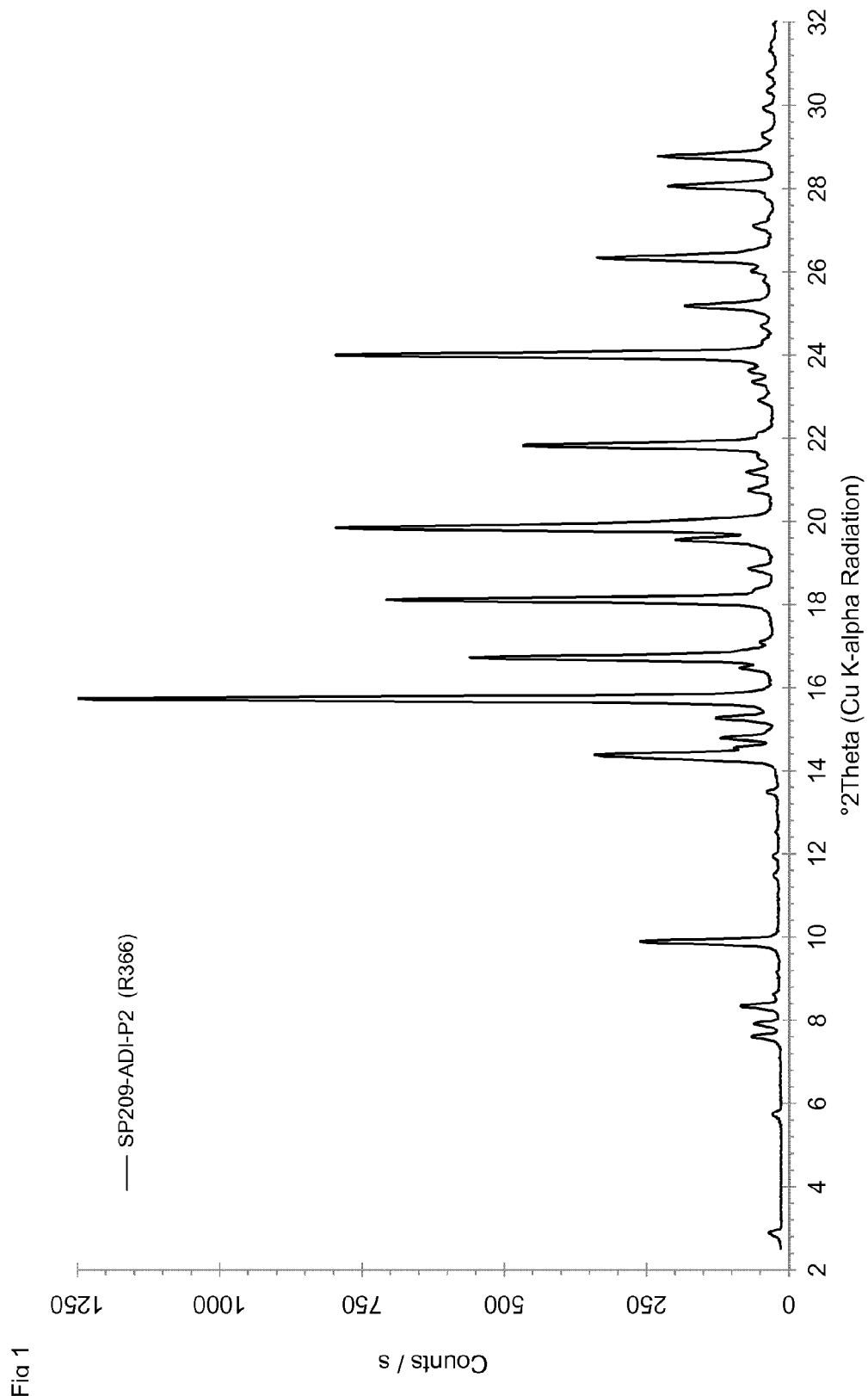
FIG. 1: Powder X-Ray Diffraction pattern of of the abiraterone acetate-adipic acid co-crystal (example 1b).
Figure 2:
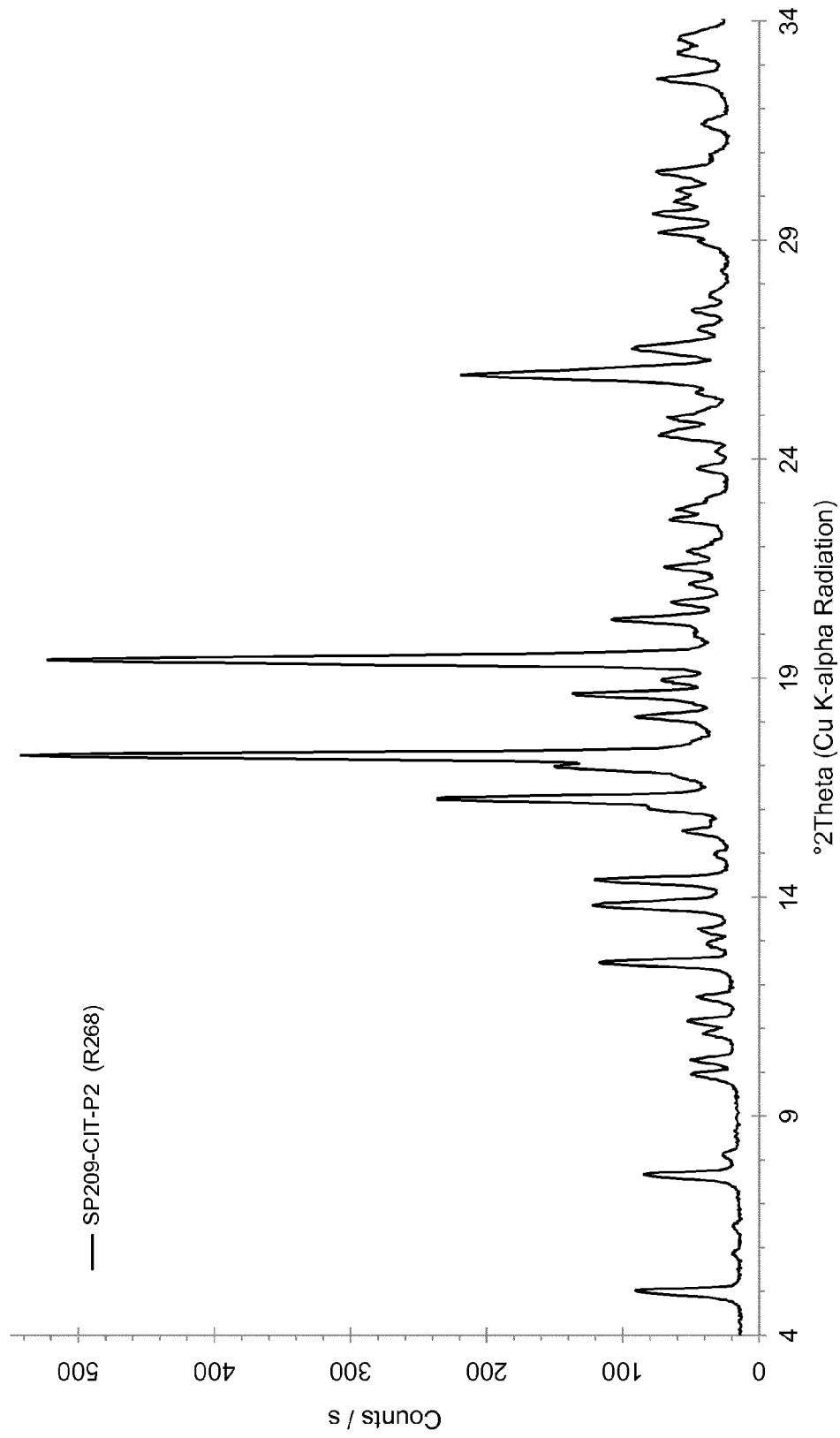
FIG. 2: Powder X-Ray Diffraction pattern of the abiraterone acetate-citric acid salt (example 2).
Figure 3:
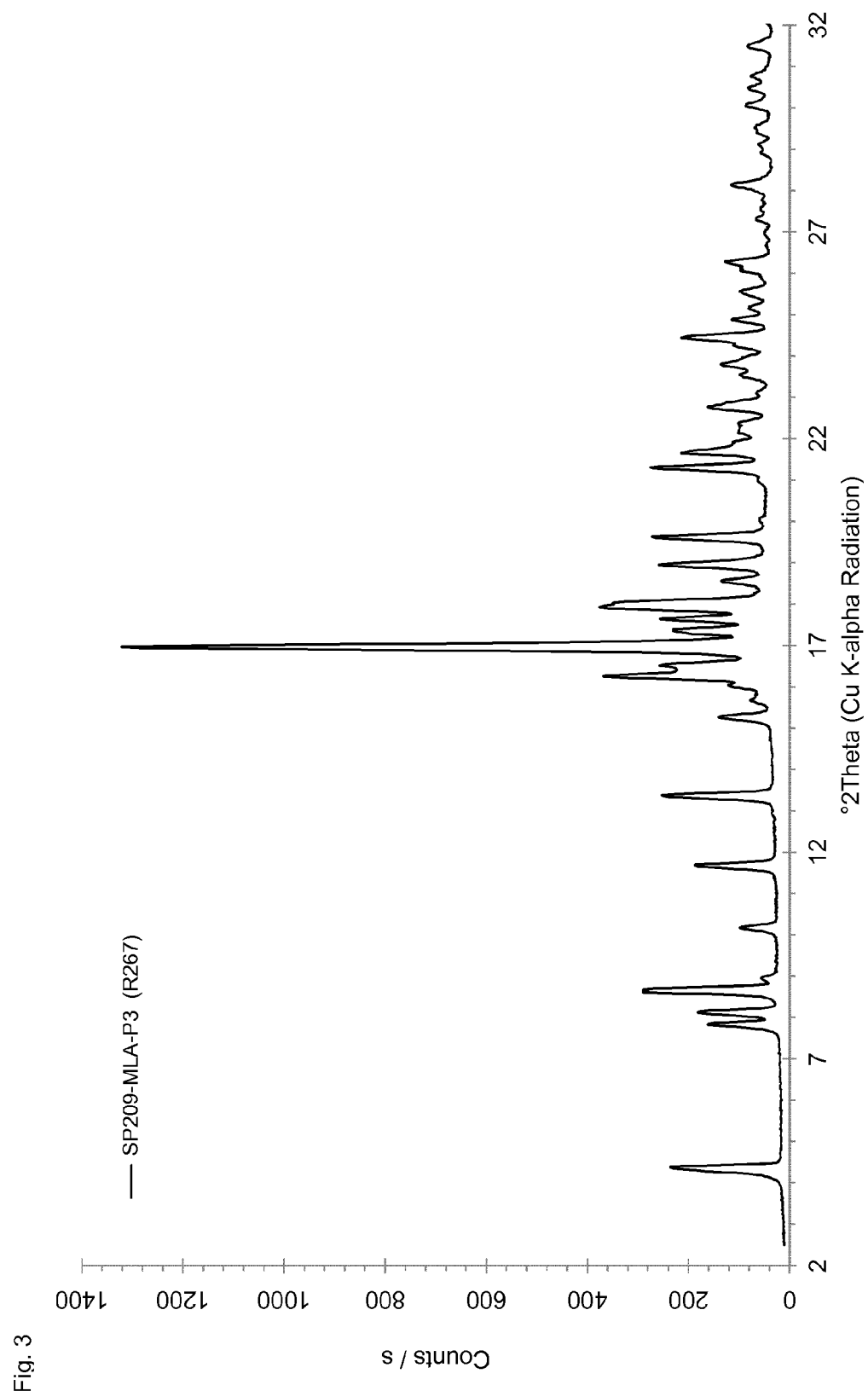
FIG. 3: Powder X-Ray Diffraction pattern of the abiraterone acetate-D,L-malic acid salt (example 3).
Figure 4A:
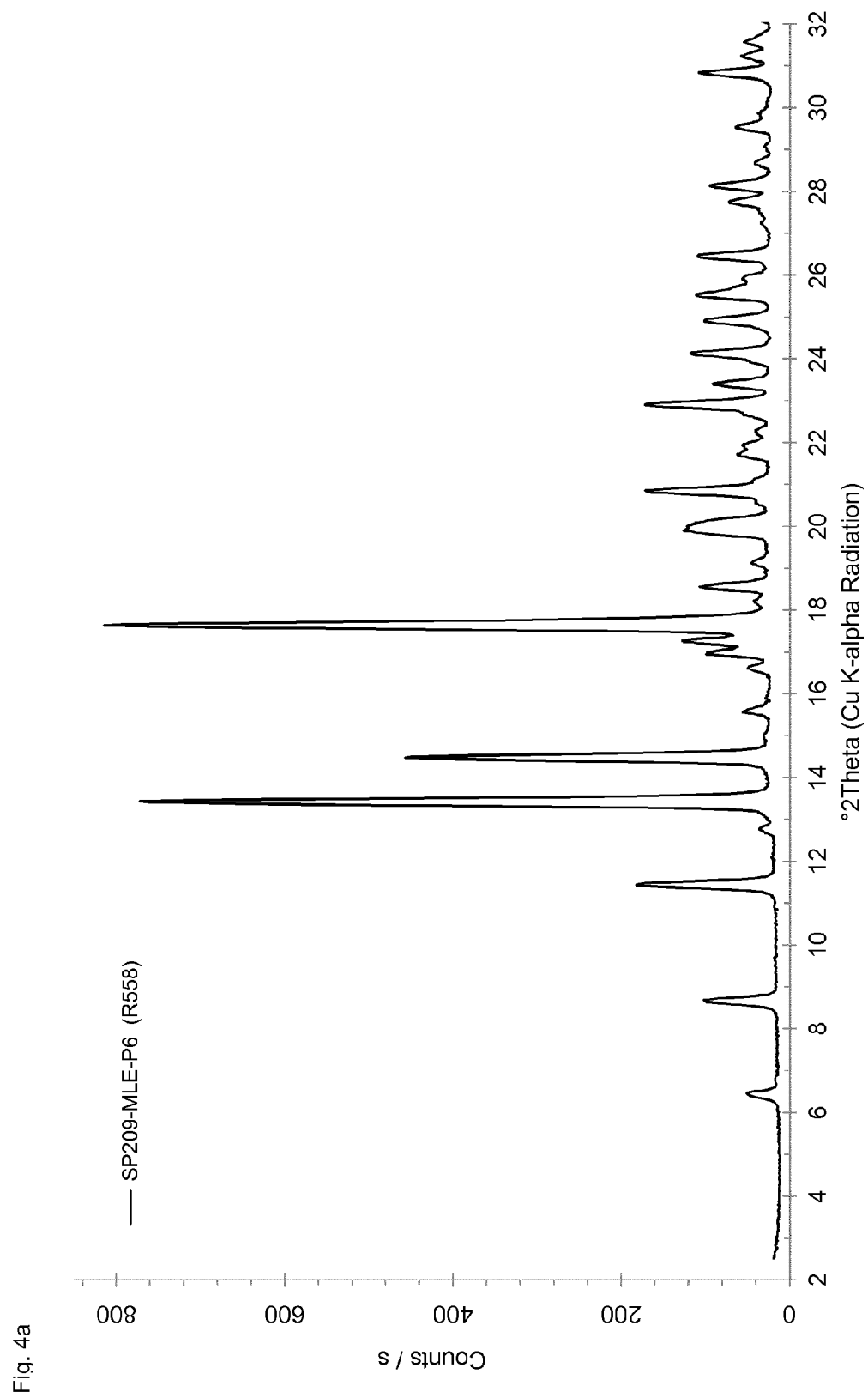
FIG. 4a: Powder X-Ray Diffraction pattern of abiraterone acetate-maleate form A.
Figure 4B:
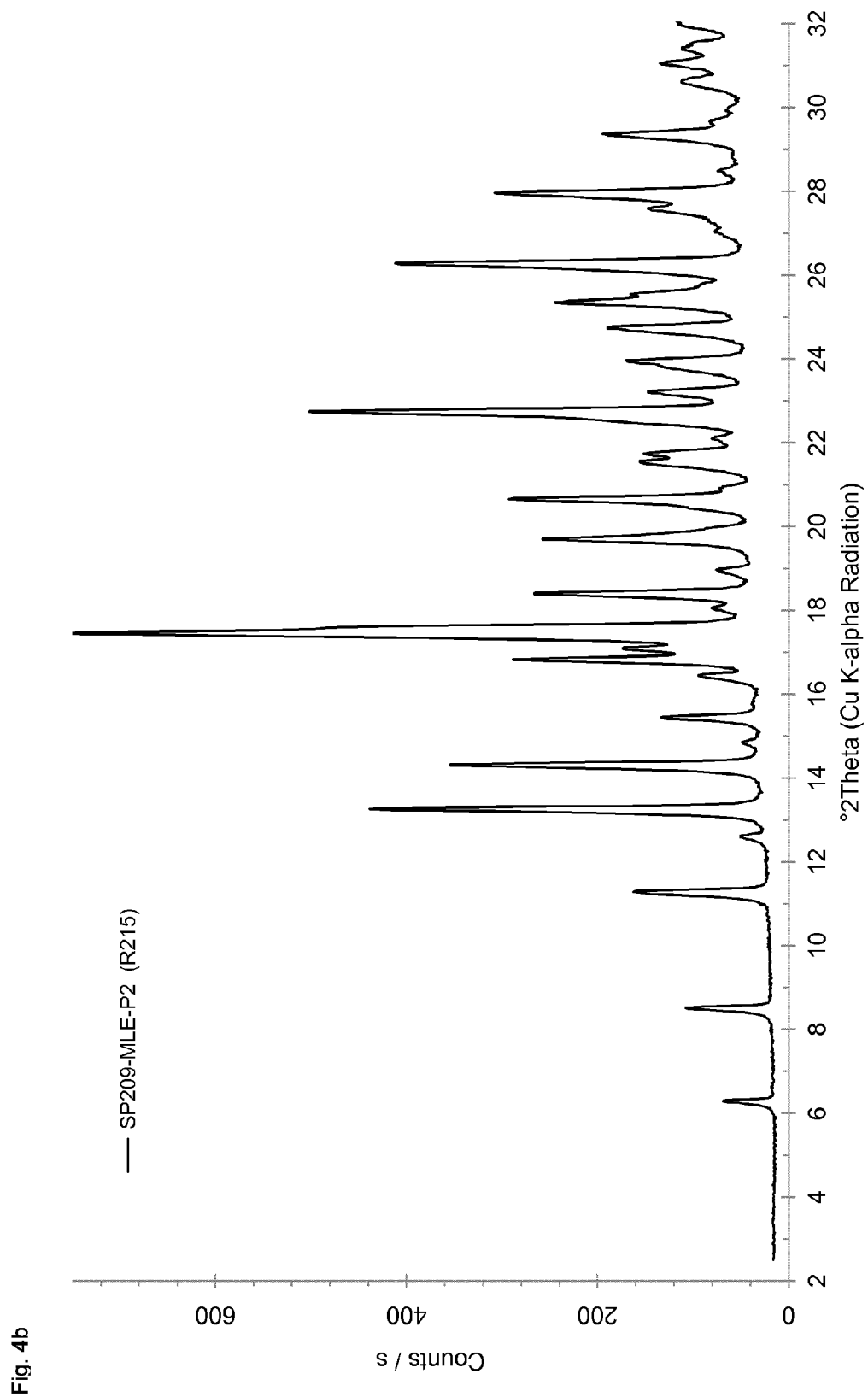
FIG. 4b: Powder X-Ray Diffraction pattern of abiraterone acetate-maleate form B.
Figure 4C:
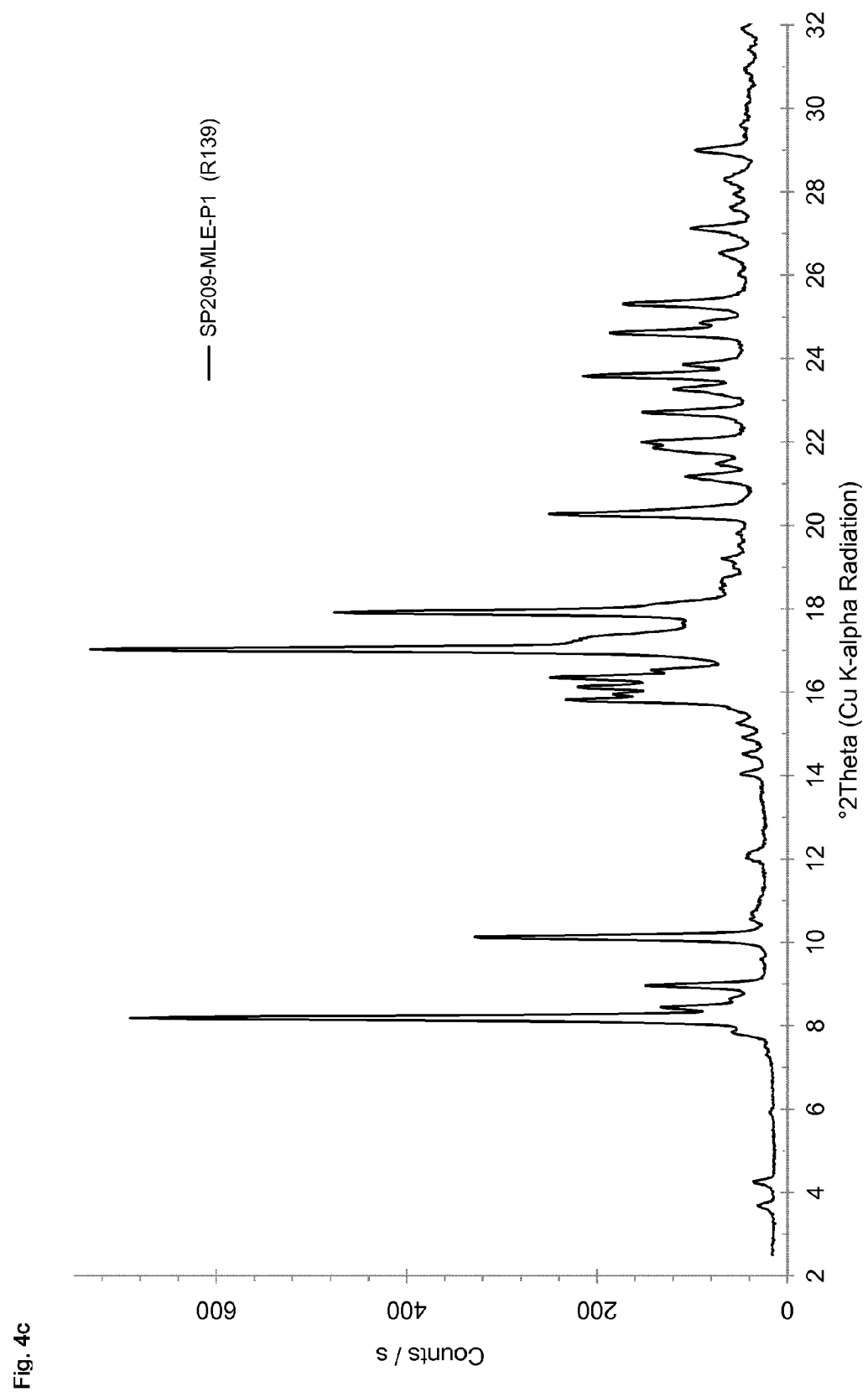
FIG. 4c: Powder X-Ray Diffraction pattern of abiraterone acetate-maleate form C.
Figure 4D:
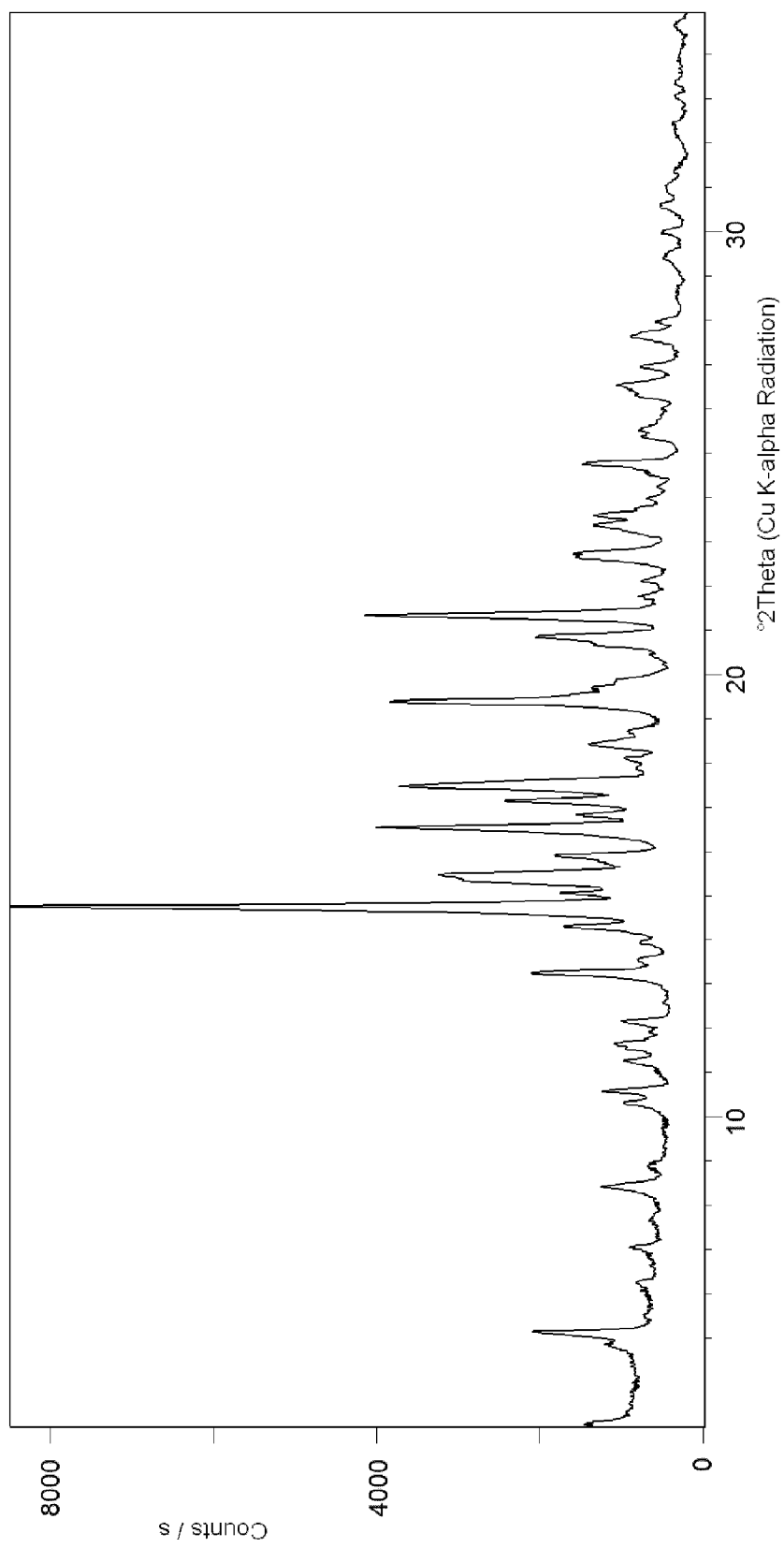
FIG. 4d: Powder X-Ray Diffraction pattern of abiraterone acetate-maleate form D.
Figure 5A:
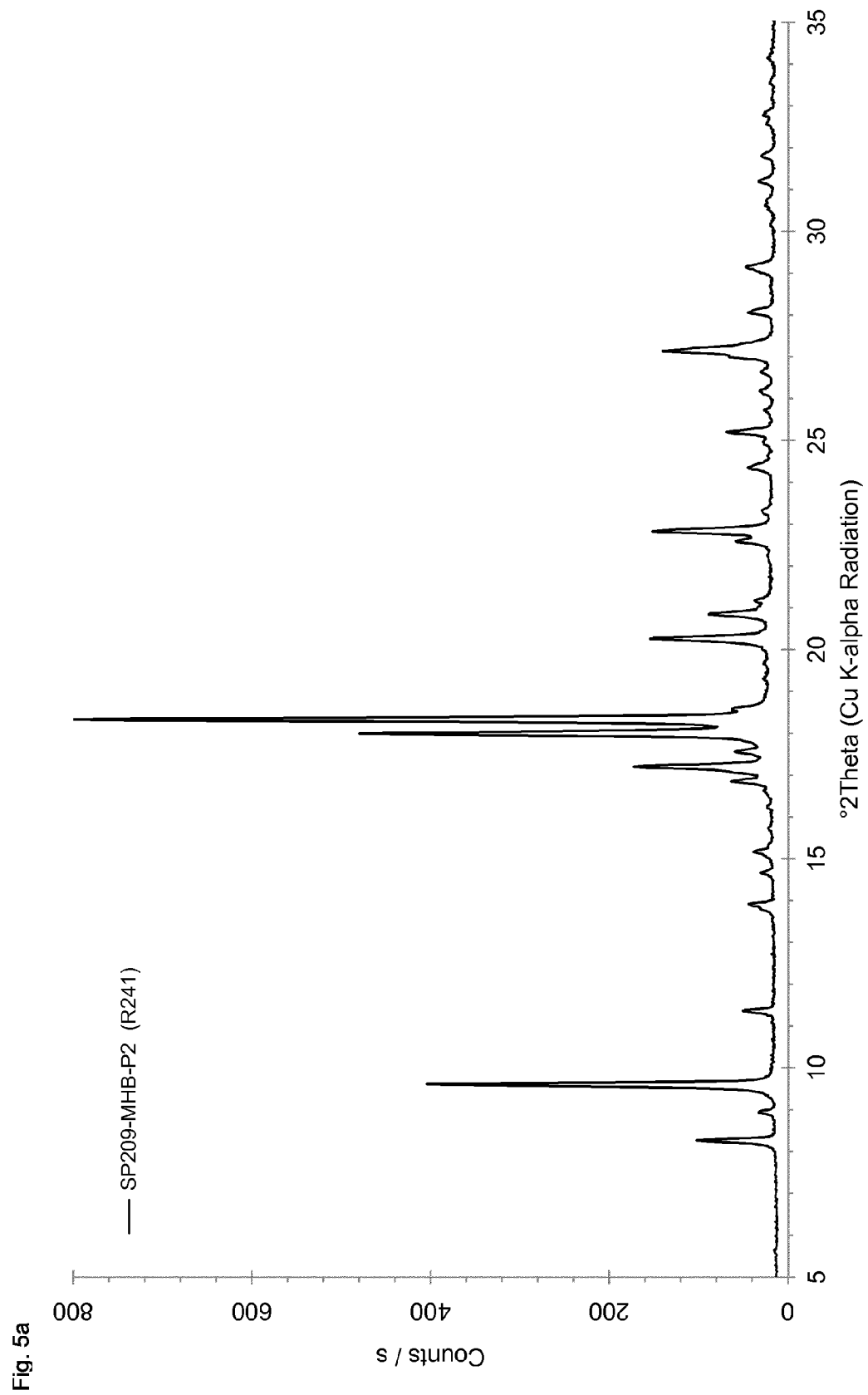
FIG. 5a: Powder X-Ray Diffraction pattern of the abiraterone acetate-Methyl-4-Hydroxy Benzoate (form A of example 5).
Figure 5B:
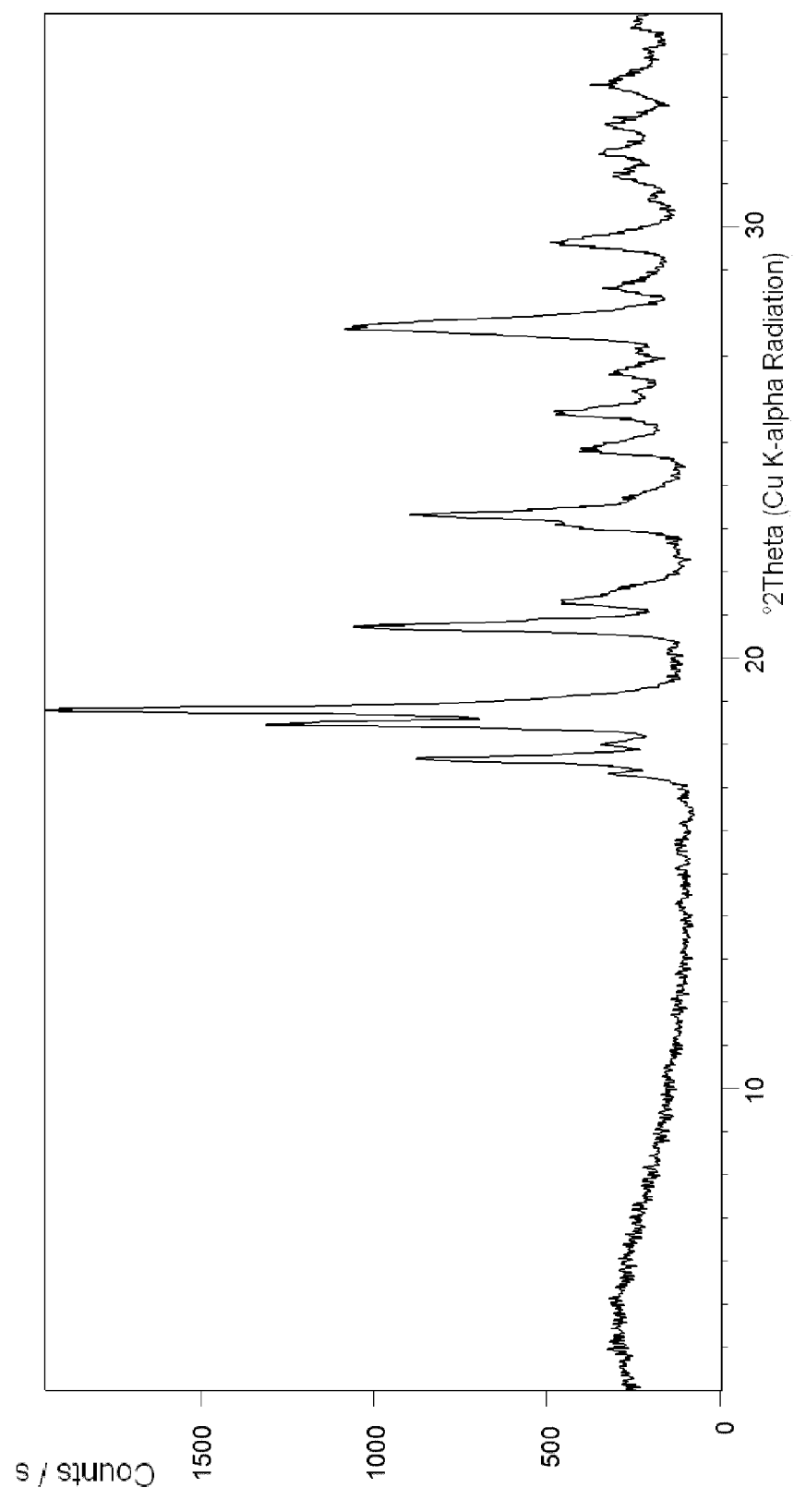
FIG. 5b: Powder X-Ray Diffraction pattern of the abiraterone acetate-Methyl-4-Hydroxy Benzoate (form B).
Figure 5C:
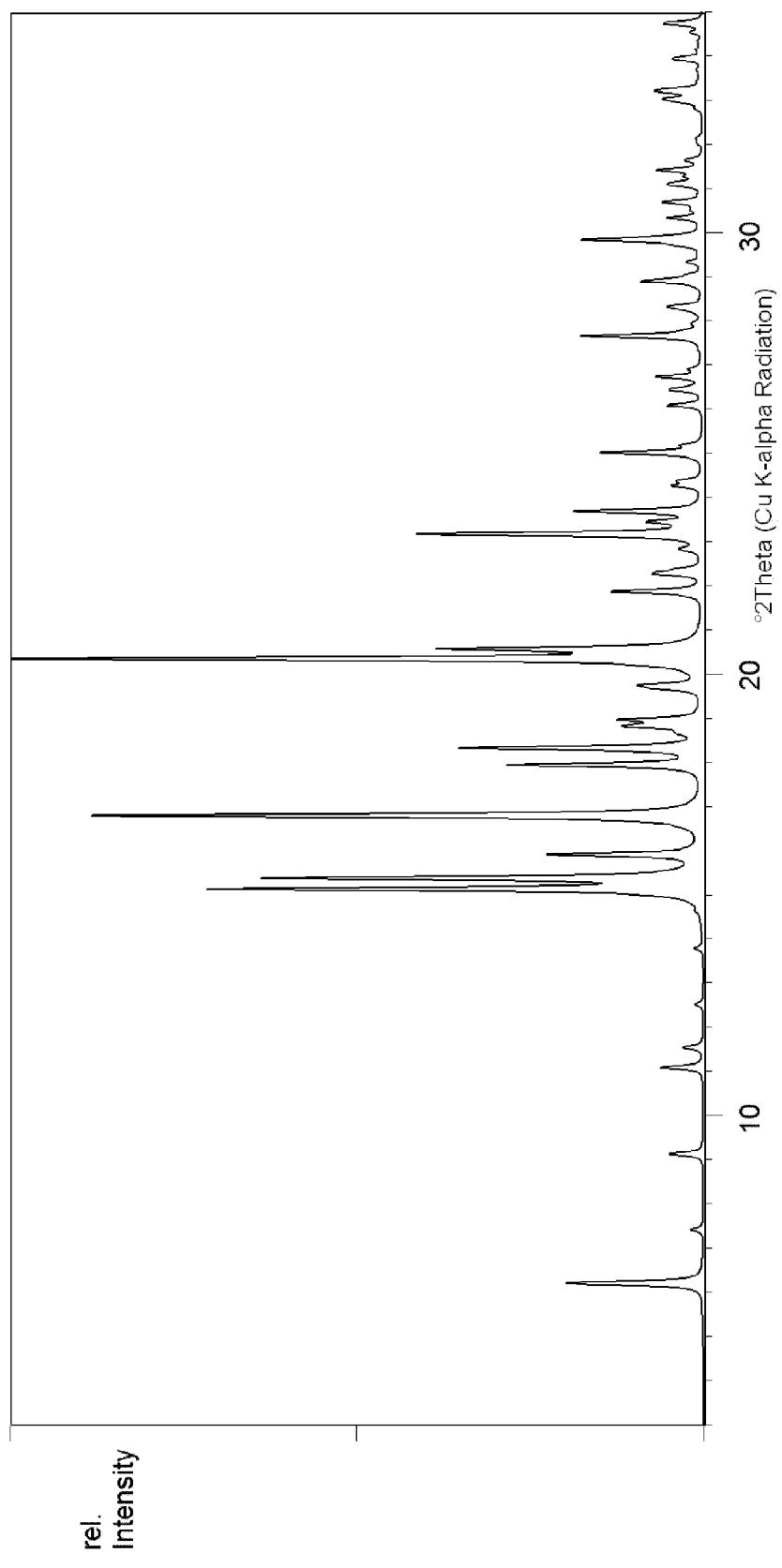
FIG. 5c: Powder X-Ray Diffraction pattern of the abiraterone acetate-Methyl-4-Hydroxy Benzoate (form C) at 100 K as calculated from single crystal data of Table 5c.
Figure 6:
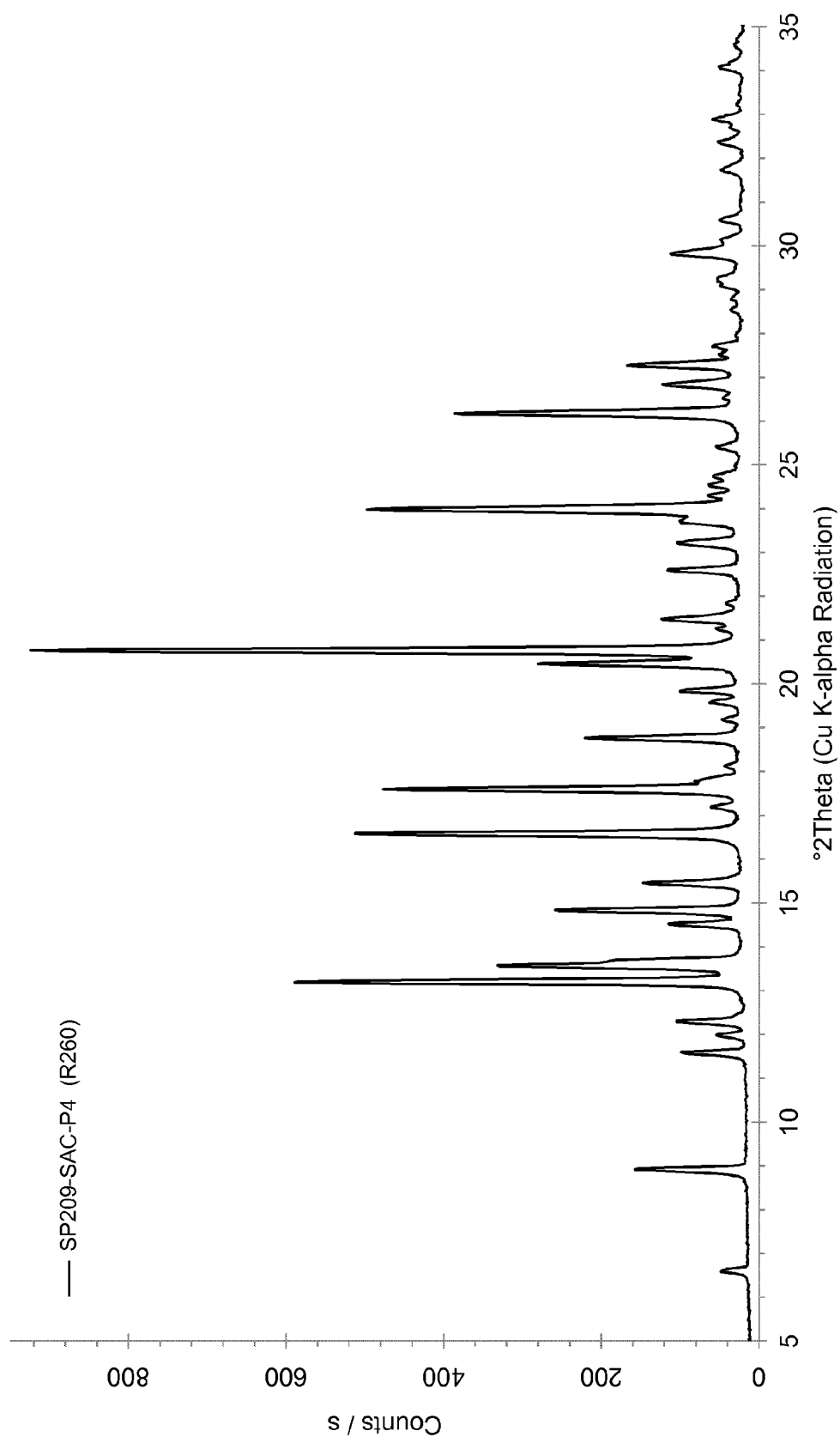
FIG. 6: Powder X-Ray Diffraction pattern of the abiraterone acetate-saccharin salt (example 6).
Figure 7A:
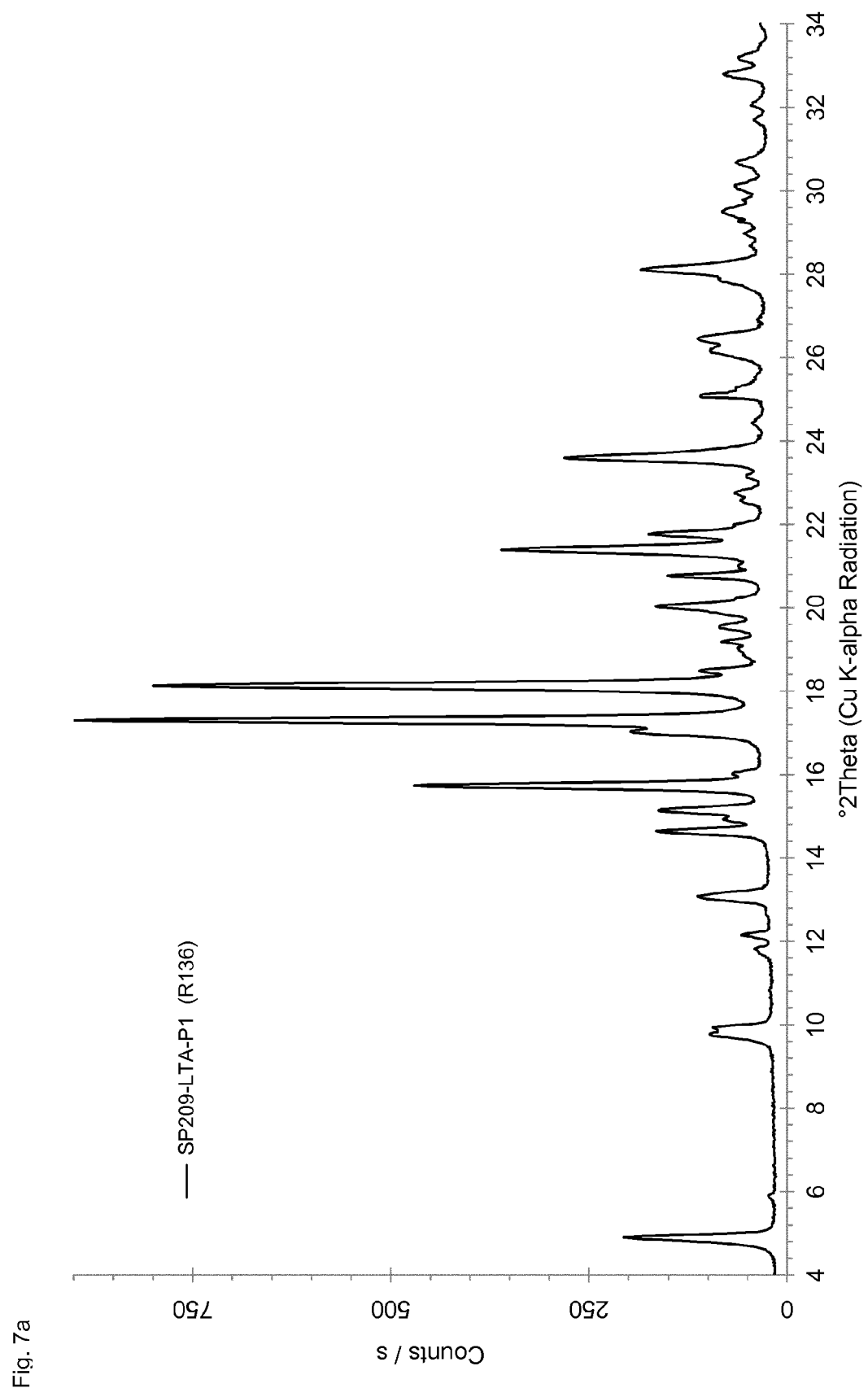
FIG. 7a: Powder X-Ray Diffraction pattern of abiraterone acetate-L-tartrate form A.
Figure 7B:
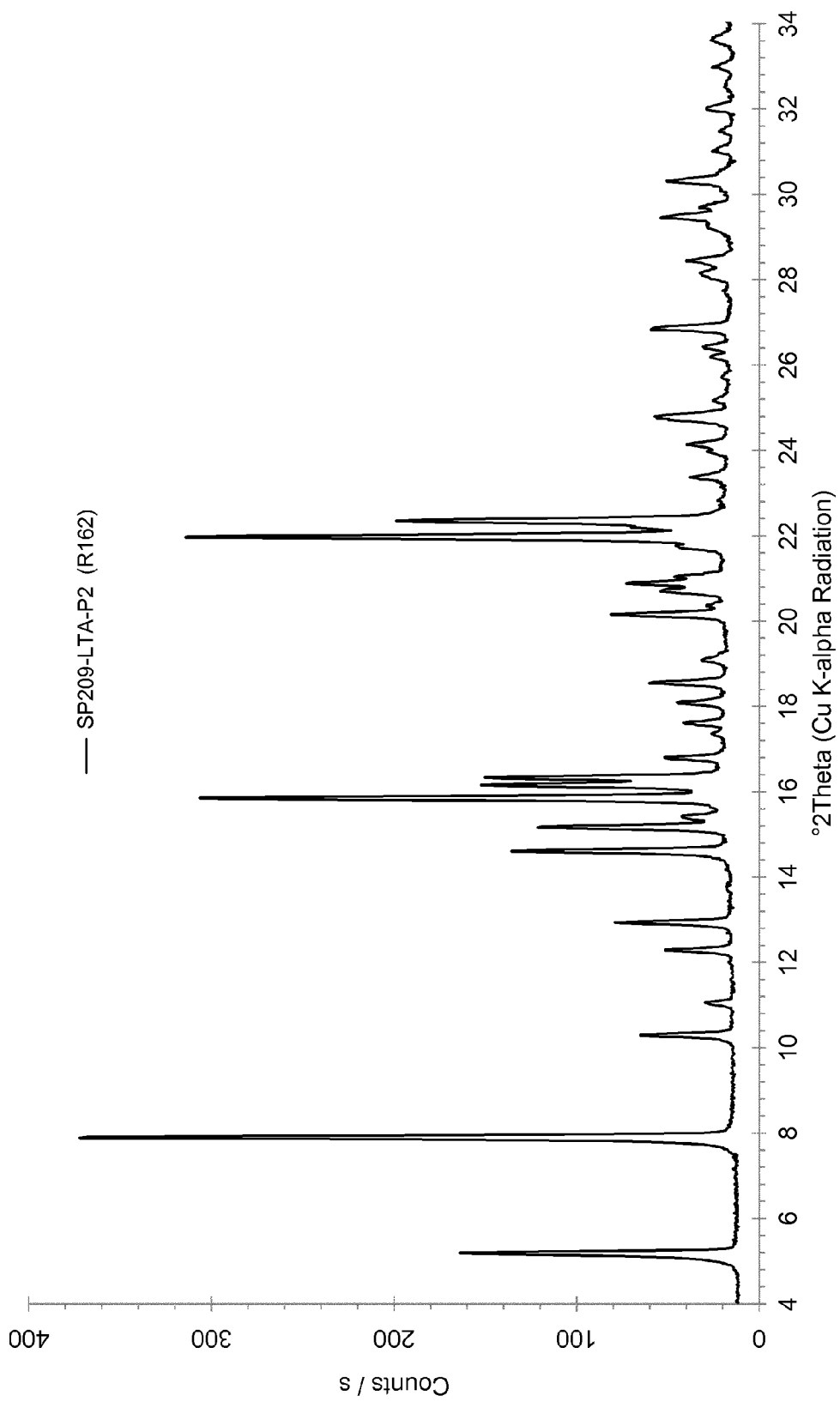
FIG. 7b: Powder X-Ray Diffraction pattern of abiraterone acetate-L-tartrate form B.
Figure 7C:
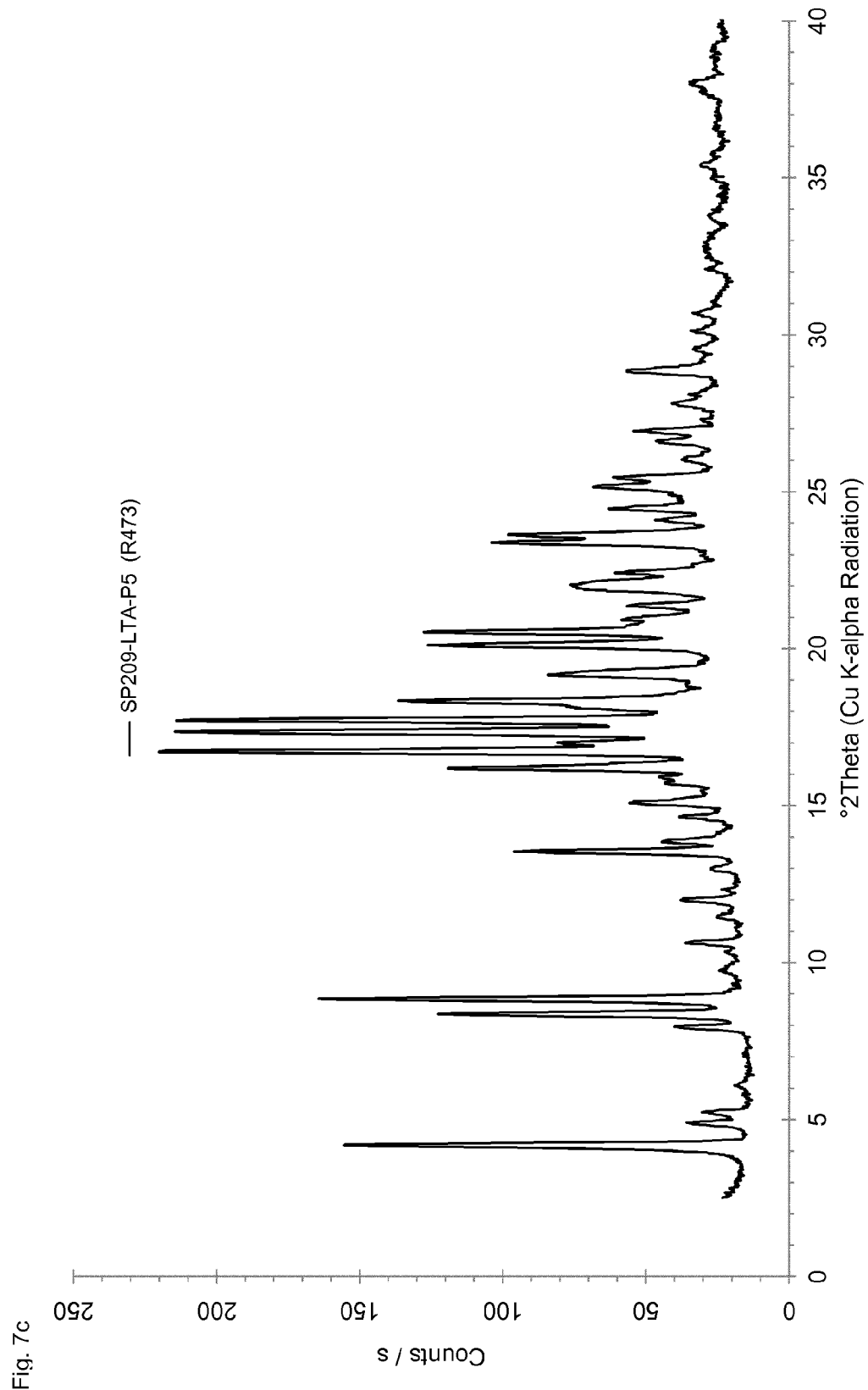
FIG. 7c: Powder X-Ray Diffraction pattern of abiraterone acetate-L-tartrate form C.
Figure 8:
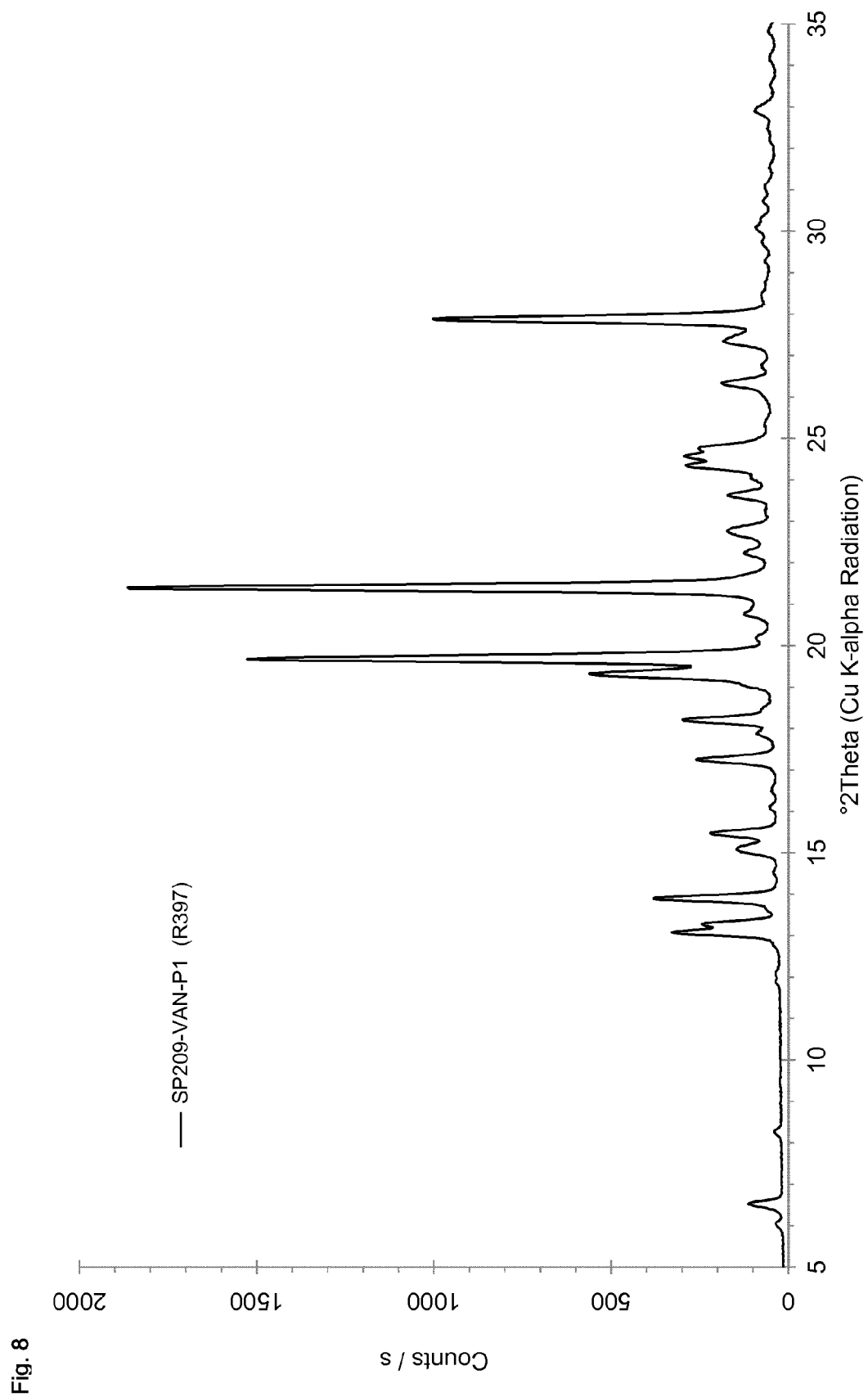
FIG. 8: Powder X-Ray Diffraction pattern of of the abiraterone acetate-vanillic acid co-crystal (example 8).

The invention claimed is:

1. A pharmaceutical composition, comprising:
   a crystalline material or a multicomponent molecular crystal; and
   a pharmaceutically acceptable carrier or diluent,
   wherein the crystalline material or the multicomponent molecular crystal comprises (3β)-17-(pyridin-3-yl)androsta-5,16-dien-3-yl acetate and an organic acid selected from the group consisting of, methyl-4-hydroxy benzoate, saccharin, vanillic acid, adipic acid and maleic acid, within the same crystalline phase, and
   wherein, in the crystalline material or the multicomponent molecular crystal, a molar ratio of (3β)-17-(pyridin-3-yl)androsta-5,16-dien-3-yl acetate to the organic acid within the same crystalline phase ranges from 2.1:1 to 1:2.1.

2. The pharmaceutical composition of claim 1, further comprising:
   at least one of citric acid and ascorbic acid as an additional component which is not part of the same crystalline phase of the crystalline material or the multicomponent molecular crystal.

3. The pharmaceutical composition of claim 1, comprising:
   a crystalline material or a multicomponent molecular crystal of (3β)-17-(pyridin-3-yl)androsta-5,16-dien-3-yl acetate and an organic acid as a coformer;
   wherein the coformer is methyl-4-hydroxy benzoate and the crystalline phase comprising (3β)-17-(pyridin-3-yl)androsta-5,16-dien-3-yl acetate and the coformer is form A exhibiting a X-ray powder diffraction pattern with the characteristic peaks, expressed in d-values (Å), at 10.7, 9.2, 7.8, 5.15, 4.93, 4.84, 4.38, 3.89, and 3.28, form B exhibiting a X-ray powder diffraction pattern with the characteristic peaks, expressed in d-values (Å), at 5.02, 4.80, 4.72, 4.29, 4.17, 3.81, 3.59, 3.47, 3.23, and 3.02, or form C exhibiting at a temperature of 100 K a X-ray powder diffraction pattern with the characteristic peaks, expressed in d-values (Å), at 6.2, 15.1, 15.4, 16.8, 20.3, and 23.2;
   or
   the coformer is saccharin and the crystalline phase comprising (3β)-17-(pyridin-3-yl)androsta-5,16-dien-3-yl acetate and the coformer exhibits a X-ray powder diffraction pattern with the characteristic peaks, expressed in d-values (Å), at 13.5, 10.0, 6.7, 6.5, 5.99, 5.74, 5.36, 5.05, 4.35, 4.28, 3.72, and 3.41;
   or
   the coformer is vanillic acid and the crystalline phase comprising (3β)-17-(pyridin-3-yl)androsta-5,16-dien-3-yl acetate and the coformer exhibits a X-ray powder diffraction pattern with the characteristic peaks, expressed in d-values (Å), at 13.5, 6.8, 6.4, 4.51, 4.15, and 3.20;
   or
   the coformer is adipic acid and the crystalline phase comprising (3β)-17-(pyridin-3-yl)androsta-5,16-dien-3-yl acetate and the coformer exhibits a X-ray powder diffraction pattern with the characteristic peaks, expressed in d-values (Å), at 9.0, 6.2, 5.63, 5.30, 4.90, 4.47, 4.07, and 3.71;
   or
   the coformer is maleic acid and the crystalline phase comprising (3β)-17-(pyridin-3-yl)androsta-5,16-dien-3-yl acetate and the coformer is form A exhibiting a X-ray powder diffraction pattern with the characteristic peaks, expressed in d-values (Å), at 13.7, 10.2, 7.7, 6.6, 6.1, 5.03, 4.46, 4.26, and 3.88, form B exhibiting a X-ray powder diffraction pattern with the characteristic peaks, expressed in d-values (Å), at 14.1, 10.4, 7.8, 6.7, 6.2, 5.74, 5.27, 5.08, 5.04, 4.82, 4.51, 4.30, 3.91, and 3.39, form C exhibiting a X-ray powder diffraction pattern with the characteristic peaks, expressed in d-values (Å), at 24.0, 20.8, 10.8, 8.7, 5.61, 5.42, 5.36, 5.21, 4.95, 4.38, and 3.77, or form D exhibiting a X-ray powder diffraction pattern with the characteristic peaks, expressed in d-values (Å), at 17.2, 6.7, 6.0, 5.36, 5.08, 4.58, 4.17, and 3.59;
   wherein the d-values are as detectable under standard conditions.

4. A crystalline material or multicomponent molecular crystal, comprising:
   (3β)-17-(pyridin-3-yl)androsta-5,16-dien-3-yl acetate; and
   an organic acid selected from the group consisting of, methyl-4-hydroxy benzoate, saccharin, vanillic acid, adipic acid, and maleic acid,
   wherein (3β)-17-(pyridin-3-yl)androsta-5,16-dien-3-yl acetate and the organic acid are included within the same crystalline phase, and
   wherein, in the crystalline material or the multicomponent molecular crystal, a molar ratio of (3β)-17-(pyridin-3-yl)androsta-5,16-dien-3-yl acetate to the organic acid within the same crystalline phase ranges from 2.1:1 to 1:2.1.

5. A process for preparing the multicomponent molecular crystal of claim 4, comprising:
   a) combining abiraterone acetate and the organic acid in a suitable solvent such that a mixture is prepared;
   b) agitating the mixture; and
   c) separating a solid material and drying the solid material,
   wherein, the agitating optionally comprises adding seed crystals to the mixture, and
   wherein, a molar ratio of (3β)-17-(pyridin-3-yl)androsta-5,16-dien-3-yl acetate to the organic acid ranges from 2.1:1 to 1:2.1.

6. The pharmaceutical composition of claim 1, wherein the pharmaceutical composition is solid.

* * * * *